US009603592B2

(12) United States Patent
Chin et al.

(10) Patent No.: US 9,603,592 B2
(45) Date of Patent: Mar. 28, 2017

(54) LAPAROSCOPIC SUTURE DEVICE WITH AUTOLOADING AND SUTURE CAPTURE

(71) Applicant: Surgimatix, Inc., Elk Grove Village, IL (US)

(72) Inventors: Wai N. Chin, Glenview, IL (US); James Orrico, Chicago, IL (US); Gary M. Kobylewski, Hoffman Estates, IL (US); Jafar S. Hasan, Oak Brook, IL (US)

(73) Assignee: Surgimatix, Inc., Elk Grove Village, IL (US)

( * ) Notice: Subject to any disclaimer, the term of this patent is extended or adjusted under 35 U.S.C. 154(b) by 256 days.

(21) Appl. No.: 14/497,936

(22) Filed: Sep. 26, 2014

(65) Prior Publication Data

US 2015/0088167 A1    Mar. 26, 2015

Related U.S. Application Data

(60) Provisional application No. 61/882,905, filed on Sep. 26, 2013.

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 17/06166* (2013.01);
(Continued)

(58) Field of Classification Search
CPC . A61B 17/04; A61B 17/0469; A61B 17/0482; A61B 17/06166;
(Continued)

(56) References Cited

U.S. PATENT DOCUMENTS

| 4,228,895 A | 10/1980 | Larkin |
| 5,084,057 A | 1/1992 | Green et al. |

(Continued)

FOREIGN PATENT DOCUMENTS

| JP | 05-237123 A | 9/1993 |
| JP | 2001-515750 A | 9/2001 |
| JP | 2012-526615 A | 11/2012 |

OTHER PUBLICATIONS

International Search Report for related International Application No. PCT/US14/57746; report dated Dec. 30, 2014.

*Primary Examiner* — Julian W Woo
(74) *Attorney, Agent, or Firm* — Miller, Matthias & Hull LLP

(57) ABSTRACT

A suturing device provided. The suturing device may include at least a firing aperture, a drive mechanism and an autoloading mechanism. The firing aperture may include at least one needle rotatably disposed therein configured to engage a suture for deployment. The drive mechanism may be operatively coupled to the needle and configured to advance the needle from a retracted position to an extended position during engagement, and retract the needle from the extended position to the retracted position during disengagement. The autoloading mechanism may be operatively coupled to the drive mechanism and configured to slidably retrieve and position a suture to be deployed over the firing aperture during disengagement of the drive mechanism.

22 Claims, 22 Drawing Sheets

(52) U.S. Cl.
CPC ............ *A61B 2017/0419* (2013.01); *A61B 2017/0427* (2013.01); *A61B 2017/0464* (2013.01); *A61B 2017/0472* (2013.01); *A61B 2017/0608* (2013.01); *A61B 2017/06042* (2013.01); *A61B 2017/06176* (2013.01)

(58) Field of Classification Search
CPC .... A61B 2017/0419; A61B 2017/0427; A61B 2017/0464; A61B 2017/0472; A61B 2017/06042; A61B 2017/0608; A61B 2017/06176; A61B 17/0401; A61B 2017/0417; A61B 2017/0409; A61B 2017/0404; A61B 2017/00398
USPC .................................................. 606/144–145
See application file for complete search history.

(56) References Cited

U.S. PATENT DOCUMENTS

| | | | | |
|---|---|---|---|---|
| 5,364,408 | A | * | 11/1994 | Gordon .............. A61B 17/0469 112/169 |
| 5,470,338 | A | * | 11/1995 | Whitfield ........... A61B 17/0469 112/169 |
| 5,527,318 | A | | 6/1996 | McGarry |
| 5,527,321 | A | * | 6/1996 | Hinchliffe .......... A61B 17/0469 112/169 |
| 5,937,951 | A | | 8/1999 | Izuchukwu et al. |
| 6,955,643 | B2 | * | 10/2005 | Gellman ............ A61B 17/0469 600/104 |
| 7,833,235 | B2 | * | 11/2010 | Chu ................... A61B 17/0469 606/144 |
| 7,905,893 | B2 | | 3/2011 | Kuhns et al. |
| 2003/0233107 | A1 | | 12/2003 | Gellman et al. |
| 2007/0270637 | A1 | | 11/2007 | Takemoto et al. |

\* cited by examiner

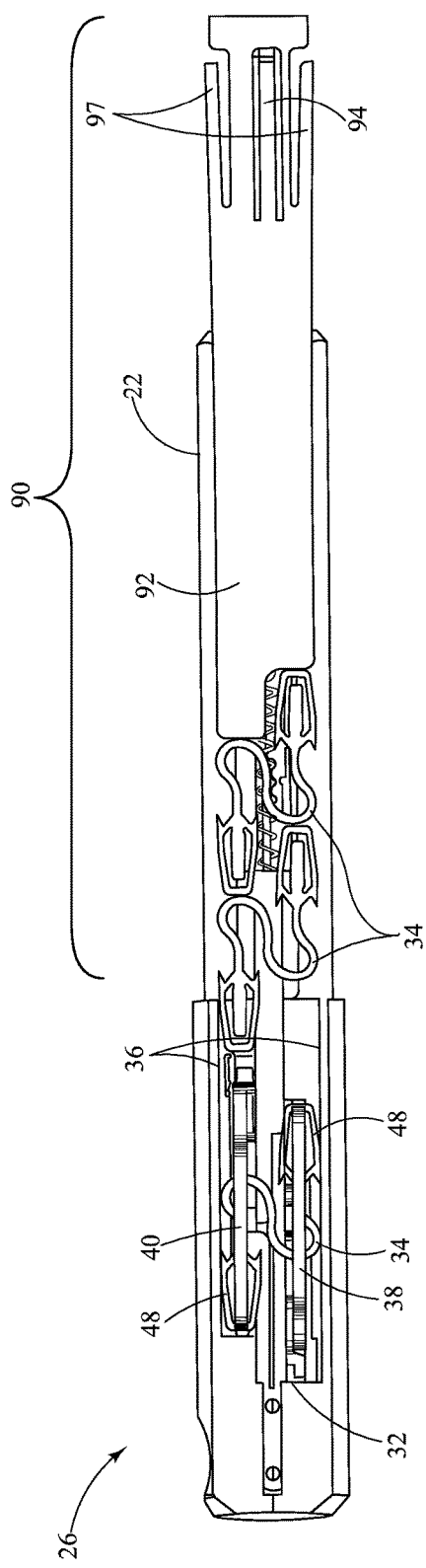
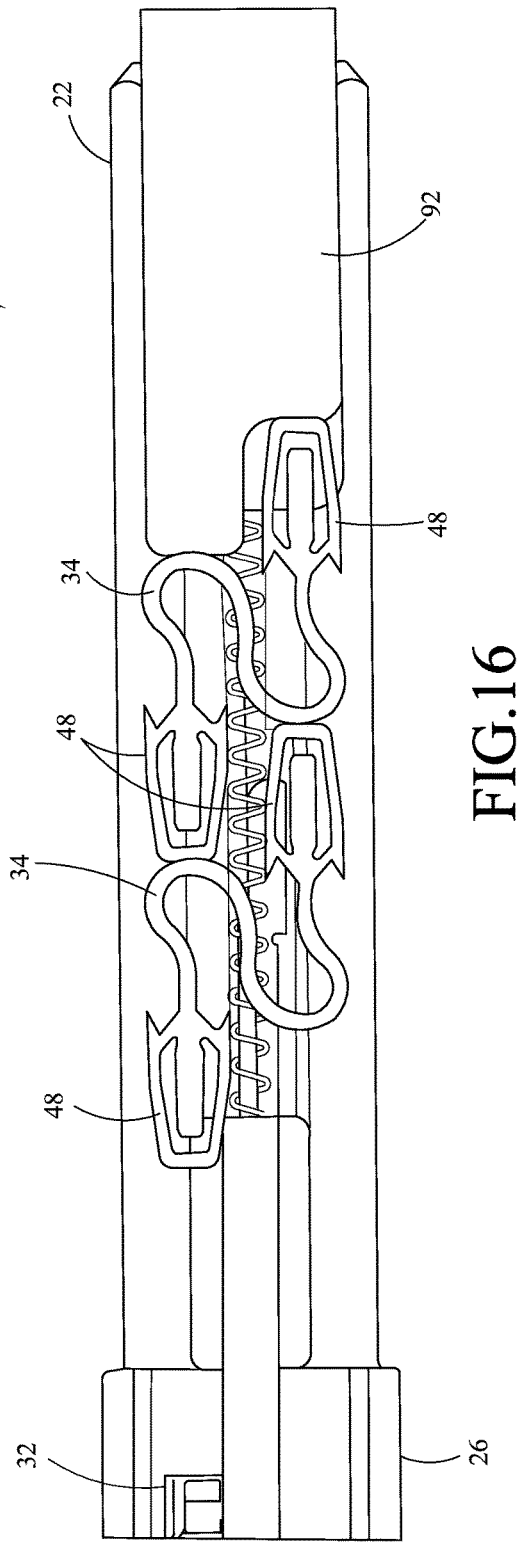
FIG.15
FIG.16

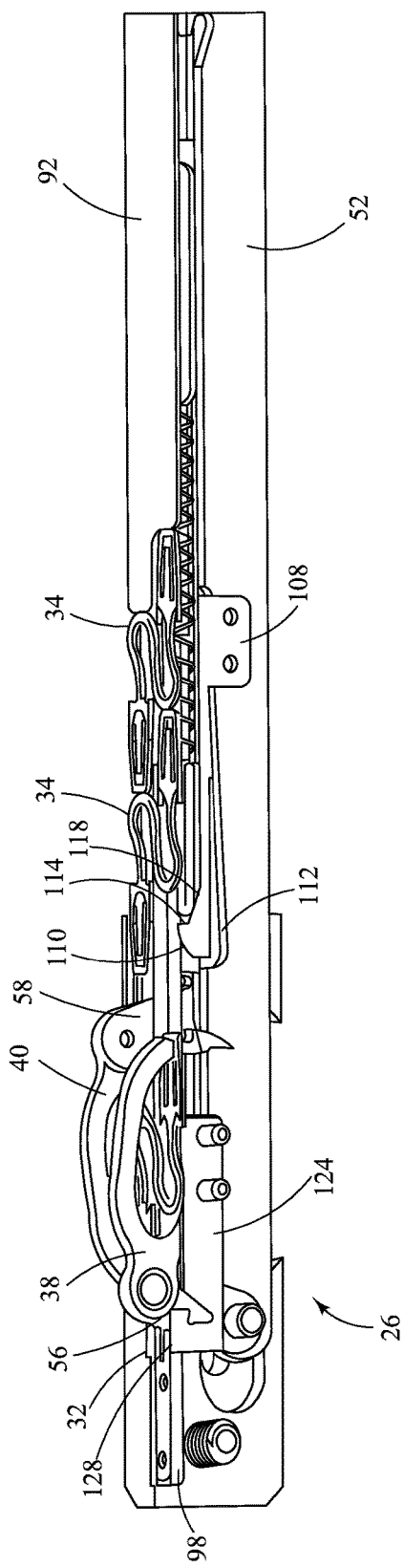
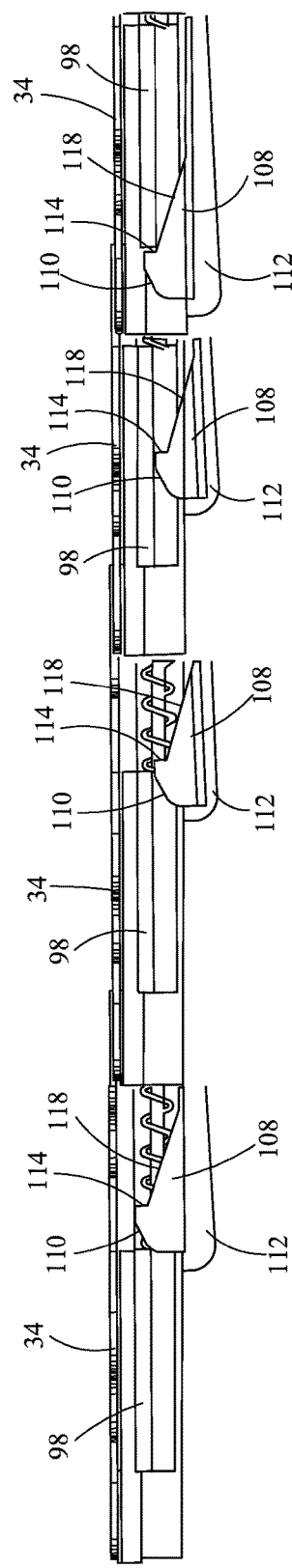
FIG.21
FIG.22 ional US patent application claiming
LAPAROSCOPIC SUTURE DEVICE WITH AUTOLOADING AND SUTURE CAPTURE

CROSS-REFERENCE TO RELATED APPLICATION

This is a non-provisional US patent application claiming priority under 35 U.S.C. §119(e) to U.S. Provisional Patent Application No. 61/882,905 filed on Sep. 26, 2013.

FIELD OF THE DISCLOSURE

The present disclosure generally relates to medical fastening devices, and more particularly, relates to sutures and suturing devices for fastening tissue and/or prosthetic material.

BACKGROUND OF THE DISCLOSURE

The fastening of tissues has long been a need in the medical industry, and correspondingly, a finite number of fastening devices have been developed for different applications and uses. Among these devices are laparoscopic fastening devices or tackers which are often used with minimally invasive procedures such as laparoscopic repair of hernias, and the like. A typical laparoscopic procedure involves the insertion of thin, elongated instruments into relatively small incisions or access ports in the abdomen to access hernia defects in the abdominal wall from the inside. Moreover, the laparoscopic instruments are used to position a prosthetic mesh over the defect and fasten the prosthetic mesh against the inner abdominal wall using tacks, or the like.

Conventional laparoscopic tackers provide a relatively thin and elongated tubular member containing deployable tacks and having an end-firing mechanism positioned at the distal tip thereof. In particular, the end-firing mechanism is configured to deploy tacks directly from the tip of the elongated member in an axial manner, and thus, ideal application suggests positioning the elongated member perpendicularly against the tissue surface to be tacked. However, due to several factors, such as the relatively rigid and elongated nature of the laparoscopic tacker, the limited locations and number of access ports available, and the typical location of hernia defects, it is difficult to position the end of the laparoscopic device squarely against the inner wall of the abdomen. In practice, a surgeon using a laparoscopic tacker typically positions the tacker with one hand, sometimes even slightly bending the instrument, while using his other hand to press against the outer wall of the abdomen in order to achieve the best possible angle for installing the tacks.

Furthermore, due to the limited access to hernia defects and the minimally invasive nature of typical hernia repairs, laparoscopic tackers tend to use simple-action type mechanisms to deploy tacks, and correspondingly, employ tacks with basic means for fastening prosthetic mesh to the inner abdominal wall. More specifically, conventional tackers employ screw-type or simple push-type actions to install tacks with threads or barbs which help embed the tacks within abdominal tissue. Over time, especially in the case of metal, coil-like tacks, these tacks may cause irritation or pain to the patient, become dislodged from the abdominal wall, or cause other complications post-surgery. To address such drawbacks associated with metal tacks, absorbable tacks have been developed and employed. Absorbable tacks are designed to be eventually absorbed by the body, and thus, cause less irritation or pain to the patient over time. However, absorbable tacks also tend to provide holding or tensile strength that is less than optimal. In such cases, suturing the hernia defects or suturing prosthetic mesh to the abdominal wall may prove to be more effective. Even still, the relatively complex nature involved with suturing makes it difficult to use sutures on hernia defects via laparoscopic or otherwise minimally invasive procedures.

Accordingly, there is a need for minimally invasive or laparoscopic means of tissue fastening or installing sutures in tissue which substantially facilitates the installation process for the surgeon or user. There is also a need for a medical fastening device which provides a more effective and reliable means for closing tissue and/or fastening prosthetic mesh to tissue. Furthermore, there is a need for a medical fastening device which employs fasteners that reduce irritation, pain, and other complications to the patient without adversely affecting tissue holding strength.

SUMMARY OF THE DISCLOSURE

In accordance with one aspect of the disclosure, a suturing device is provided. The suturing device may include at least a firing aperture, a drive mechanism and an autoloading mechanism. The firing aperture may include at least one needle rotatably disposed therein configured to engage a suture for deployment. The drive mechanism may be operatively coupled to the needle and configured to advance the needle from a retracted position to an extended position during engagement, and retract the needle from the extended position to the retracted position during disengagement. The autoloading mechanism may be operatively coupled to the drive mechanism and configured to slidably retrieve and position a suture to be deployed over the firing aperture after a prior suture has been deployed.

In accordance with another aspect of the disclosure, a suturing device is provided. The suturing device may include at least an elongate member, a drive mechanism and an autoloading mechanism. The elongate member may extend between a working end and a control end, and include a track for receiving one or more deployable sutures therein. The working end may include a firing aperture disposed in communication with the track, and a distal needle and a proximal needle rotatably disposed therein. The drive mechanism may be disposed within the elongate member and configured to operatively couple the control end with each of the distal and proximal needles. The drive mechanism may be configured to advance each of the distal and proximal needles from a retracted position to an extended position during engagement, and retract each of the distal and proximal needles from the extended position to the retracted position during disengagement. The autoloading mechanism may be disposed along the elongate member and proximate the working end. The autoloading mechanism may be operatively coupled to the drive mechanism and configured to slidably retrieve and position one of the deployable sutures over the firing aperture for deployment after a prior suture has been deployed.

In accordance with yet another aspect of the disclosure, a tissue fastener is provided. The tissue fastener may include at least an elongated filament extending between a first end and a second end, a needle guide disposed on at least one of the first and second ends configured to be at least partially engaged by a needle during deployment, one or more retention elements disposed on the needle guide configured to resist retraction through at least one of a tissue and a prosthetic material, and one or more constriction elements disposed on the needle guide configured to at least partially constrict the needle guide against the needle during deployment.

These and other aspects and features of the disclosure will be better understood upon reading the following detailed description when taken into conjunction with the accompanying drawings.

BRIEF DESCRIPTION OF THE DRAWINGS

FIG. 15 is a partial top plan view of the working end, autoloading mechanism and first and second needles of a suturing device;

FIG. 16 is a partial top plan view of the autoloading mechanism of a suturing device;

FIG. 21 is a partial perspective view of the working end, first and second needles and autoloading mechanism of a suturing device;

FIG. 22 are partial side plan views of the autoloading mechanism of a suturing device during engagement;

Figure 1:
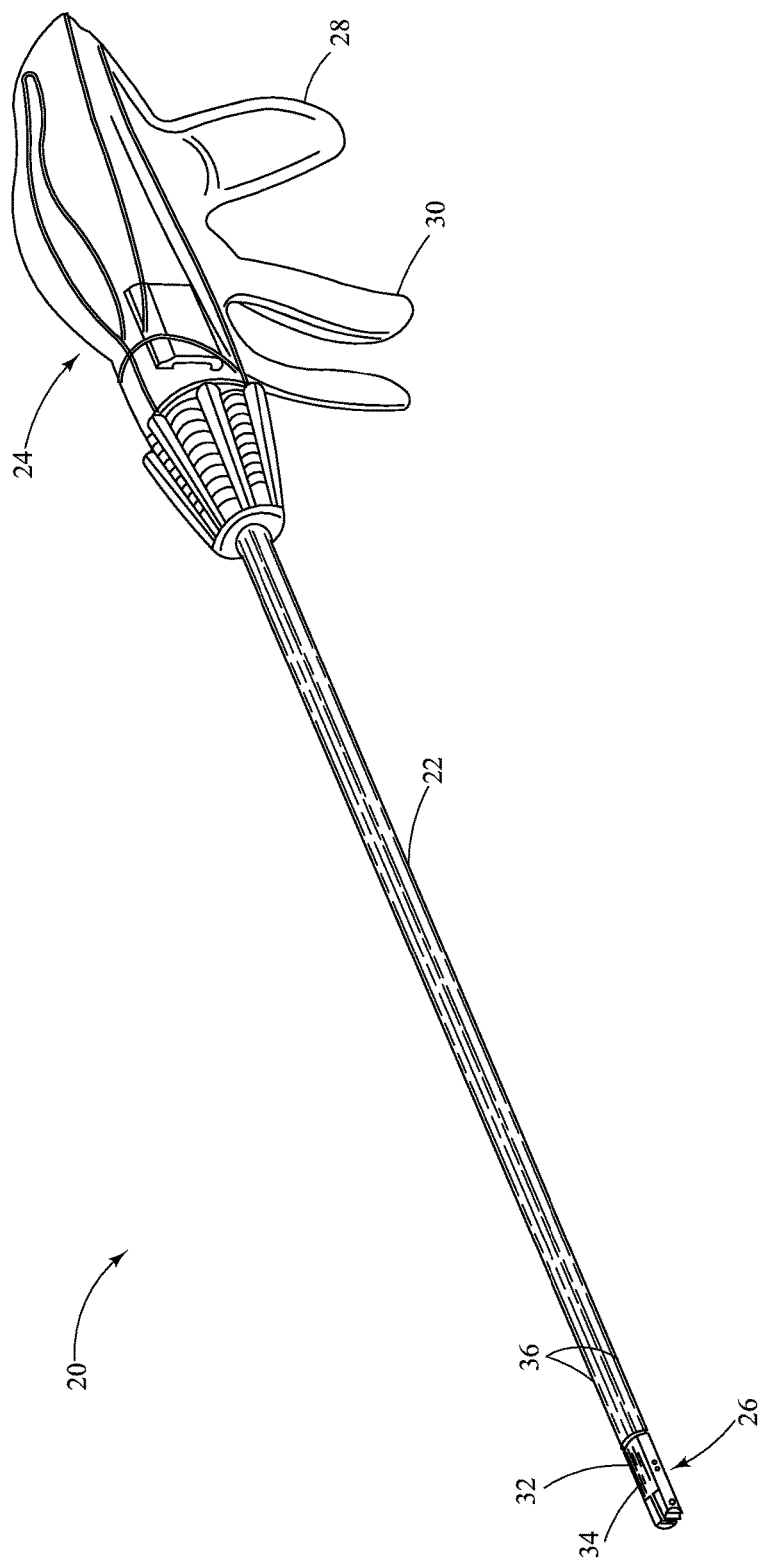
FIG. 1 is a perspective view of a suturing device constructed in accordance with the teachings of the present disclosure.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions and equivalents falling within the spirit and scope of the present disclosure.

DETAILED DESCRIPTION

Referring now to the drawings, and with specific reference to FIG. 1, a medical fastening or suturing device constructed in accordance with the teachings of the present disclosure is generally referred to by reference numeral 20. The suturing device 20, as will be described in further detail herein, may advantageously enable convenient yet effective means of providing fasteners within a surgical environment. The disclosed embodiments may additionally facilitate the installation of fasteners or sutures during minimally invasive surgical procedures, such as laparoscopic procedures, and the like. As used for laparoscopic treatment of a hernia, the embodiment of FIG. 1, for example, may be employed to reach beneath sections of tissue, within or around the abdominal region, to fasten tissues of the abdominal wall or to fasten prosthetic mesh to the abdominal wall from the inside. Although the embodiments disclosed herein demonstrate tissue fastening as applied to laparoscopic applications, it will be understood that the present disclosure may be equally or similarly applied to other medical procedures.

As shown in FIG. 1, the suturing device 20 may generally include an elongate member 22 which extends between a control end 24 disposed at a proximal end thereof, and a working end 26 disposed at a distal end thereof. The control end 24 may generally include a grip 28 as well as a triggering mechanism 30, or any other suitable means for receiving input or triggering actions from a user and converting the input or actions into a suturing action that is performed at the working end 26 of the suturing device 20. The working end 26 may generally be configured with a firing aperture 32, or a fastening interface disposed at a longitudinal side thereof, through which fasteners or sutures 34 may be deployed or installed in tissue and/or prosthetic material. Furthermore, one or more of the sutures 34 to be deployed may be provided along the elongate member 22 and distally advanced or fed toward the firing aperture 32 of the working end 26, for example, along one or more guides or tracks 36 longitudinally disposed within the elongate member 22.

Figure 2:
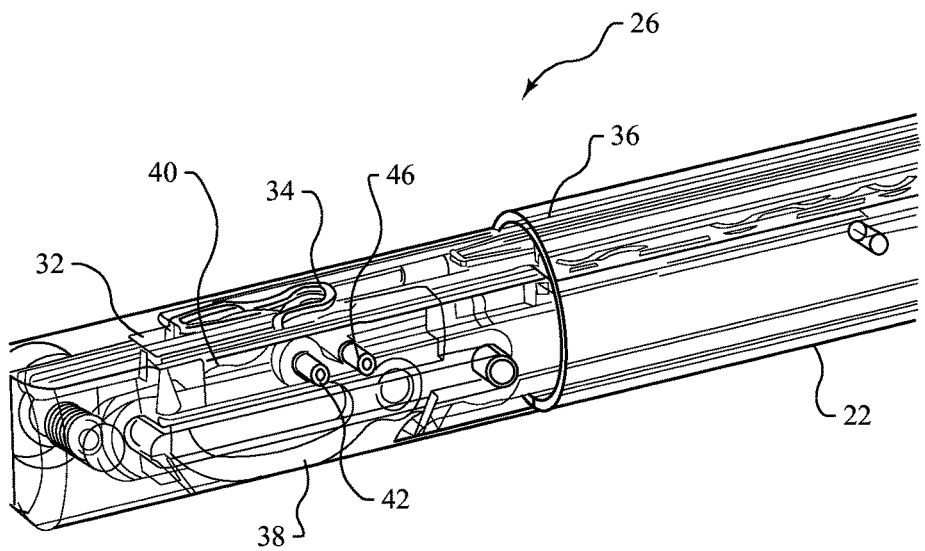
FIG. 2 is a partial perspective view of the working end of a suturing device with fully retracted first and second needles.
Figure 3:
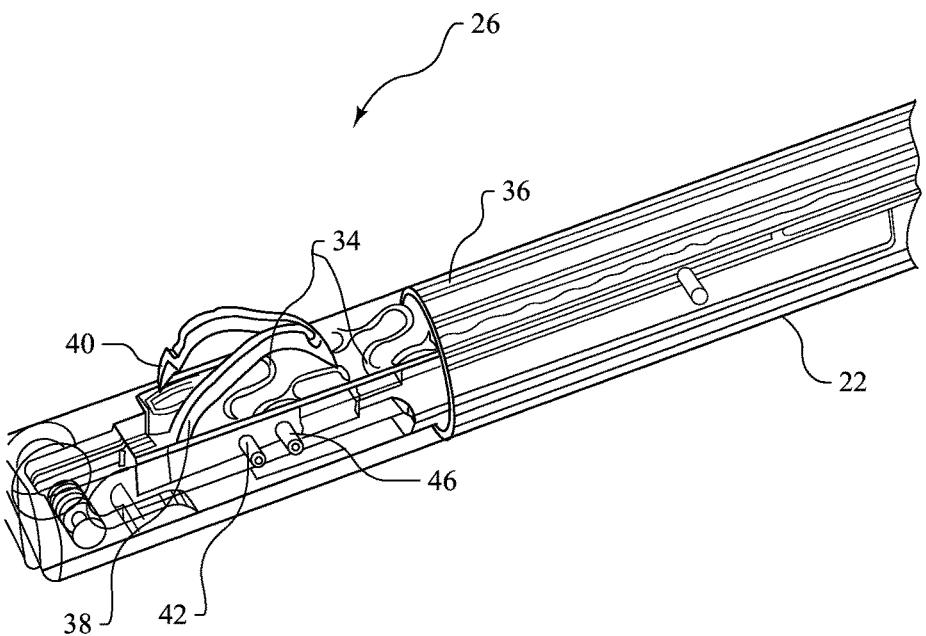
FIG. 3 is a partial perspective view of the working end of a suturing device with partially extended first and second needles.

As shown in more detail in FIGS. 2 and 3, the working end 26 of the suturing device 20 of FIG. 1 may at least partially enclose a first needle 38 and a second needle 40, each of which may be substantially concealed within the firing aperture 32 of the working end 26 in a default or fully retracted position. More specifically, the first needle 38 may be rotatably and pivotally disposed about a first fixed axis 42, and the second needle 40 may be rotatably and pivotally disposed about a second fixed axis 44. Moreover, the first axis 42 may be axially offset but substantially parallel to the second axis 44, for example, such that the first needle 38 is distally positioned relative to the suturing device 20 and the second needle 40 is proximally positioned relative to the suturing device 20. In other alternative embodiments, each of the first and second needles 38, 40 may be coaxially disposed about a common axis. In still further embodiments, a single needle or more than two needles may be disposed within the firing aperture 32 and comprise any one of a plurality of different arrangements.

Still referring to FIGS. 2 and 3, each of the first and second needles 38, 40 may be configured to rotate in opposing directions between respective retracted and extended positions. For example, during advancement, the first or distal needle 38 may be configured to proximally rotate toward the elongate member 22, while the second or proximal needle 40 may be configured to distally rotate away from the elongate member 22. Conversely, during retraction, the first needle 38 may be configured to distally rotate away from the elongate member 22, while the second needle 40 may be configured to proximally rotate toward the elongate member 22. Moreover, each of the first and second needles 38, 40 may be configured to advance and retract between respective retracted and extended positions simultaneously, or in substantially equal increments or at substantially equal rates of angular displacement. Each of the first and second needles 38, 40 may further comprise a low-profile arcuate geometry which enables the needles 38, 40 to be substantially concealed within the firing aperture 32 while in the fully retracted position, and have maximized reach during advancement. Furthermore, each arcuate needle 38, 40 may be shaped and/or otherwise configured to rotate in a cammed fashion such that, it creates a progressively tighter pull as it travels through the tissue, and thus, creates a tighter fastening of the tissue.

In addition, each of the first and second needles 38, 40 of FIGS. 2 and 3 may include one or more of needle hooks 46, grooves, tines, recesses, canted surfaces, or any other suitable structure configured to enable engagement with a fastener or suture 34, or one or more needle guides 48 thereof. As shown in FIGS. 2 and 3, for example, a hook 46 may be disposed on an outer edge of each of the first and second needles 38, 40 and configured to engage with a needle guide 48 of a suture 34 as the respective needle 38, 40 is retracted from the fully extended position. While the embodiments of FIGS. 2 and 3 may depict the needles 38, 40 with retrograde-type hooks 46 configured to engage a suture 34 during retraction, it will be understood that other configurations may be equally or similarly employed, such as antegrade-type hooks configured to engage a suture 34 during advancement, or the like. In still further alternatives, one or more hooks may be disposed on an inner edge of each of the needles 38, 40.

Turning now to FIGS. 4-9, more detailed drawings of the first and second needles 38, 40 are provided illustrating the relative rotational positions thereof as the needles 38, 40 are advanced from fully retracted positions to fully extended positions. As shown, each of the first and second needles 38, 40 may be operatively coupled to a drive mechanism 50 that is configured to advance the needles 38, 40 from the retracted positions to the extended positions during an engagement of the drive mechanism 50 received via the control end 24 of the suturing device 20, and conversely, to retract the needles 38, 40 from the extended positions to the retracted positions during a disengagement of the drive mechanism 50 received via the control end 24. Furthermore, the drive mechanism 50 may include a multi-bar linkage, such as a three-bar linkage, or the like, which operatively couples the control end 24 to each of the first and second needles 38, 40.

As shown in FIGS. 4-9, the drive mechanism 50 may include at least a first drive link 52 for driving the first needle 38 and a second drive link 54 for driving the second needle 40, each of which may be slidably disposed within the elongate member 22 and in operative communication between the control end 24 and the working end 26. The drive mechanism 50 may additionally include a first intermediate link 56 for driving the first needle 38 and a second intermediate link 58 for driving the second needle 40, each of which may configured to pivotally couple the corresponding drive link 52, 54 to the corresponding needle 38, 40. In other modifications, one or more links may be omitted or added to the drive mechanism 50. As the needles 38, 40 are opposedly arranged, the drive links 52, 54 and the intermediate links 56, 58 may be configured to be slidably and pivotally driven in substantially equal increments or rates of displacement, but in opposing directions relative to one another. For example, during advancement, the first drive link 52 of the first needle 38 may be slidably driven distally toward the working end 26 at substantially the same rate or in similar increments as the second drive link 54 of the second needle 40 being driven proximally away from the working end 26.

Figure 4:
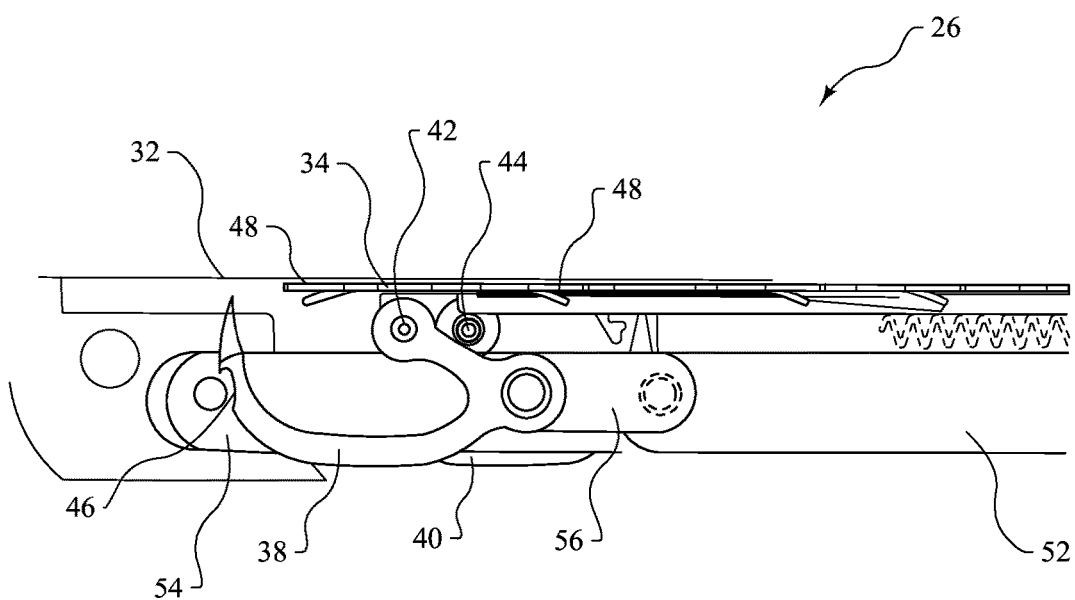
FIG. 4 is a cross-sectional side plan view of the working end of a suturing device with first and second needles disposed in the fully retracted positions.
Figure 5:
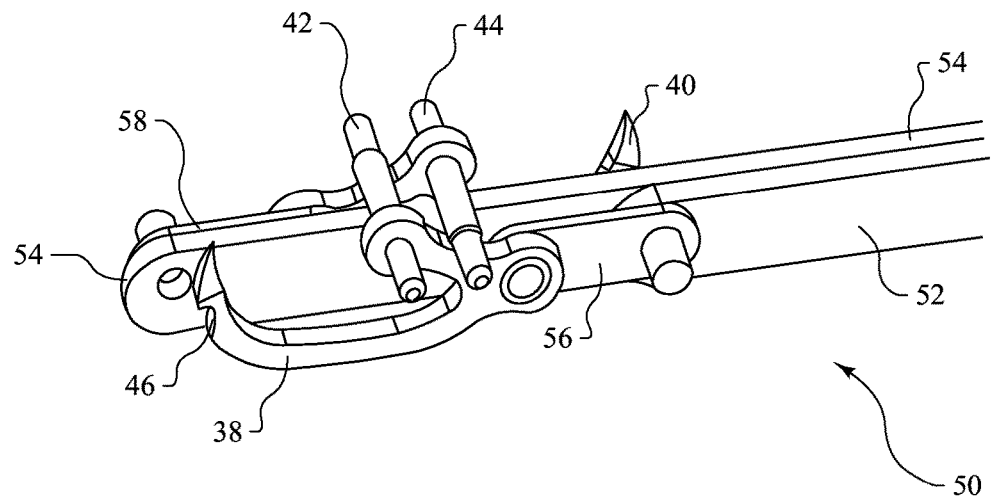
FIG. 5 is a partial perspective view of the working end of a suturing device with first and second needles disposed in the fully retracted positions.
Figure 6:
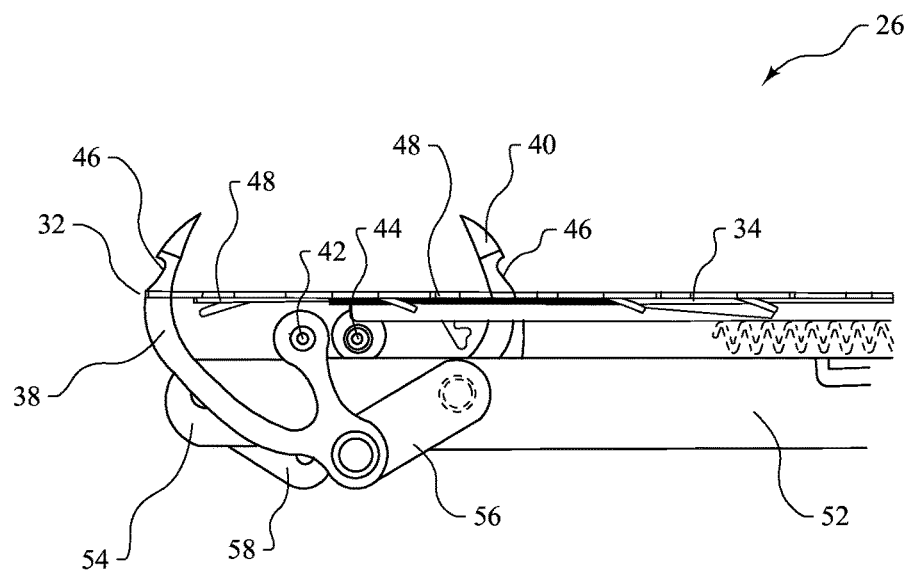
FIG. 6 is a cross-sectional side plan view of the working end of a suturing device with first and second needles disposed in partially extended positions.
Figure 7:
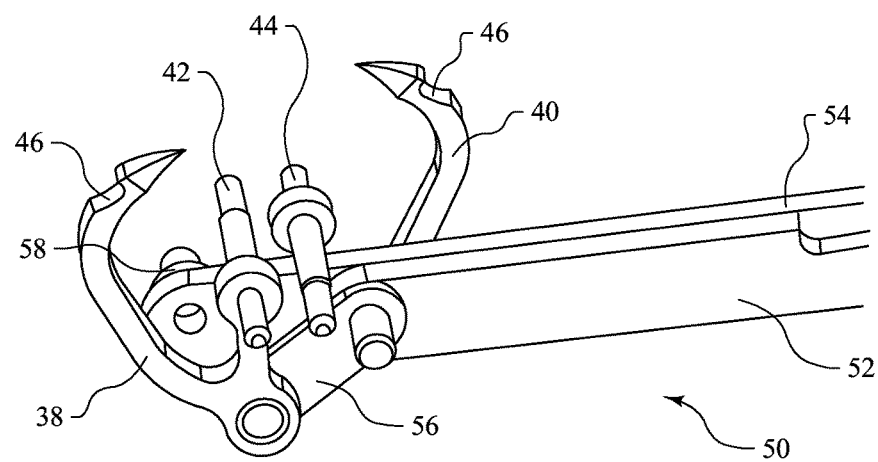
FIG. 7 is a partial perspective view of the working end of a suturing device with first and second needles disposed in partially extended positions.

In the fully retracted positions, as shown in FIGS. 4 and 5 for example, each of the first and second needles 38, 40 may be substantially concealed beneath the firing aperture 32 and within the working end 26 of the suturing device 20 so as to facilitate insertion thereof into minimal incisions or access ports, or the like. The first and second needles 38, 40 may further include a low-profile geometry which enables the working end 26 of the suturing device 20 as well as the access ports to be generally smaller in size. During advancement or during engagement of the drive mechanism 50, as shown in FIGS. 6 and 7 for example, the first drive link 52 may drive or push the first intermediate link 56 toward the distal end of the firing aperture 32 thereby causing the first needle 38 to rotate about the first fixed axis 42 and upwardly extend from the distal end of the firing aperture 32, while the second drive link 54 may drive or pull the second intermediate link 58 toward the proximal end of the firing aperture 32 thereby causing the second needle 40 to rotate about the second fixed axis 44 and upwardly extend from the proximal end of the firing aperture 32. Moreover, the drive mechanism 50 may be configured to rotatably extend the needles 38, 40 such that the reach of each needle 38, 40 is maximally extended during advancement even with a low-profile geometry so as to sufficiently penetrate tissue and/or prosthetic material to be fastened or sutured.

Figure 8:
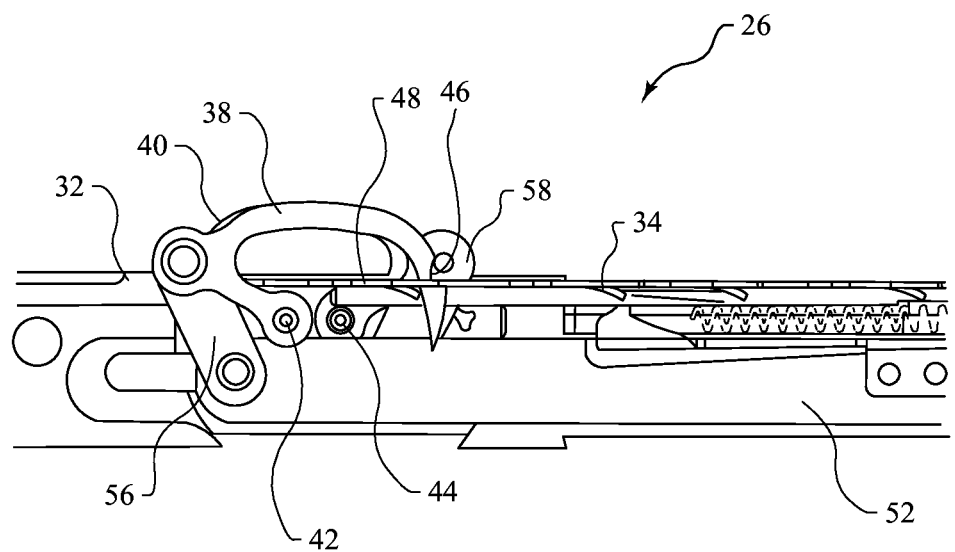
FIG. 8 is a cross-sectional side plan view of the working end of a suturing device with first and second needles disposed in fully extended positions.
Figure 9:
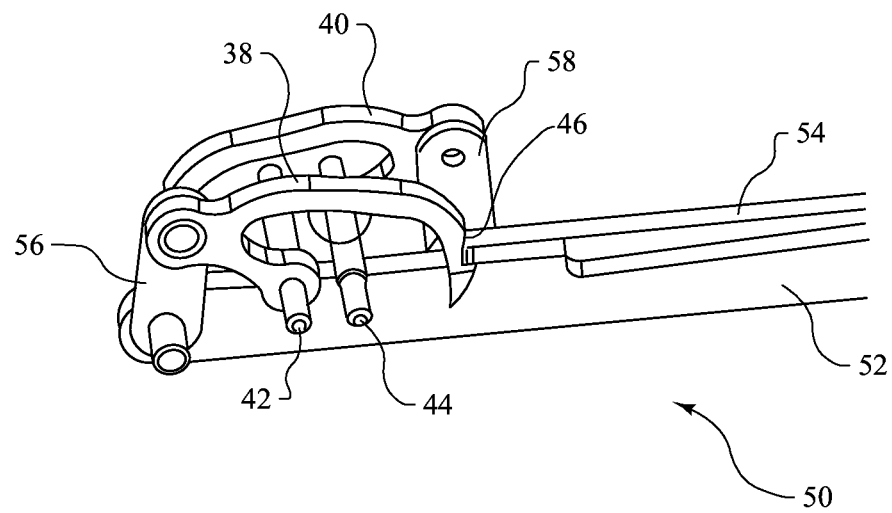
FIG. 9 is a partial perspective view of the working end of a suturing device with first and second needles disposed in fully extended positions.

The drive mechanism 50 may continue advancing each of the first and second needles 38, 40 until the needles 38, 40 respectively reach the fully extended positions, as shown for example in FIGS. 8 and 9. In particular, the drive mechanism 50 may be configured such that each of the first and second needles 38, 40 extend until at least one or more of the hooks 46 thereof engage with a fastener or suture 34 for deployment. For example, positioning of the first and second needles 38, 40, the drive mechanism 50, the firing aperture 32, and the sutures 34 may be configured such that retrograde-type hooks 46 on the outer edges of the needles 38, 40 are able to fully engage with one or more corresponding needle guides 48 of a given suture 34. In other alternatives, each of the needles 38, 40 may employ a retrograde-type hook disposed on the inner edge thereof, an antegrade-type hook disposed on the outer edge thereof, an antegrade-type hook disposed on the inner edge thereof, or any other suitable variation thereof, to which each of the drive mechanism 50, the firing aperture 32, and the like, may be modified to enable sufficient engagement with the corresponding needle guide 48 of a given suture 34.

Once the first and second needles 38, 40 respectively reach the fully extended positions thereof as shown for example in FIGS. 8 and 9, and once a suture 34 is fully engaged, the drive mechanism 50 may be released or disengaged, so as to retract the needles 38, 40 and deploy the engaged suture 34 within tissue and/or prosthetic material to be fastened. Moreover, the needles 38, 40 may be retracted toward the positions shown in FIGS. 4 and 5 by substantially reversing the drive mechanism 50. During retraction or during disengagement of the drive mechanism 50, for example, the first drive link 52 may drive or pull the first intermediate link 56 toward the proximal end of the firing aperture 32 thereby causing the first needle 38 to rotate in reverse about the first fixed axis 42 and downwardly retract into the distal end of the firing aperture 32. Correspondingly, the second drive link 54 may drive or push the second intermediate link 58 toward the distal end of the firing aperture 32 thereby causing the second needle 40 to rotate in reverse about the second fixed axis 44 and downwardly retract into the proximal end of the firing aperture 32. Furthermore, each of the first and second needles 38, 40 may be retracted until the needles 38, 40 return to the fully retracted positions of FIGS. 4 and 5 and until a previously engaged suture 34 is completely deployed and released therefrom, at which point the needles 38, 40 may be advanced again to engage with a new suture 34 for deployment.

While one possible implementation is provided in the drawings, other drive mechanisms and configurations therefor will be apparent to those skilled in the art without departing from the scope of the appended claims. For example, in other modifications, the suturing device 20 may employ more than two needles which, for instance, partially oppose one another, or alternatively, rotate in like manner and direction relative to one another. In alternative modifications, the needles 38, 40 may be configured to be rotated sequentially rather than simultaneously relative to one another, and/or configured to be rotated at non-identical rates of angular displacement relative to one another. In additional modifications, the needles 38, 40 may be configured to rotate about a common axis rather than axially offset. In further modifications, the suturing device 20 may provide a needle that is configured to rotate about an axis that is parallel, or otherwise generally not perpendicular, to the elongate member 22. In still further modifications, the working end 26 of the suturing device 20 may be articulated, such as pivotable or otherwise movable, relative to the elongate member 22 about one or more axes.

Figure 10:
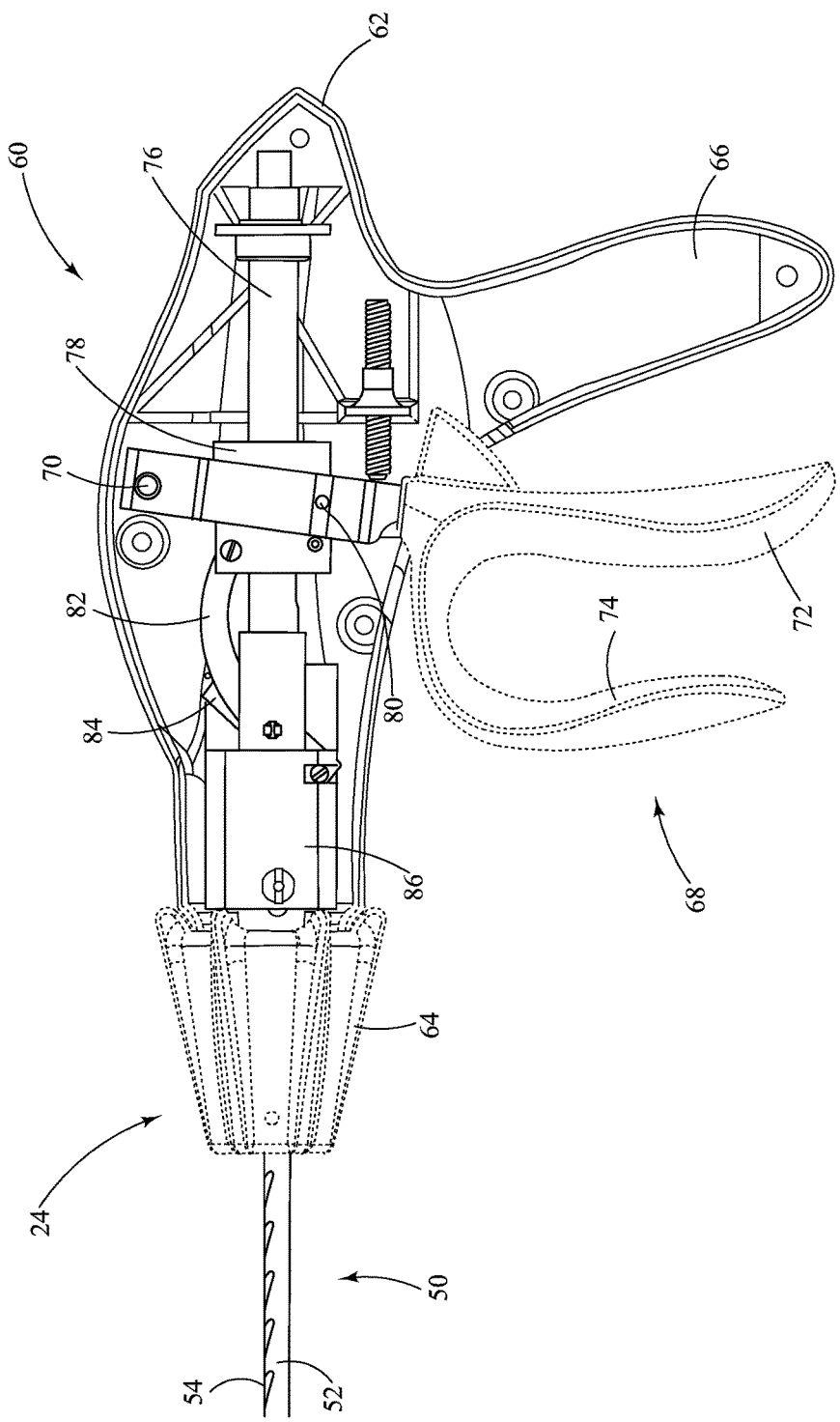
FIG. 10 is a cross-sectional side plan view of the control end and triggering mechanism of a suturing device.
Figure 11:
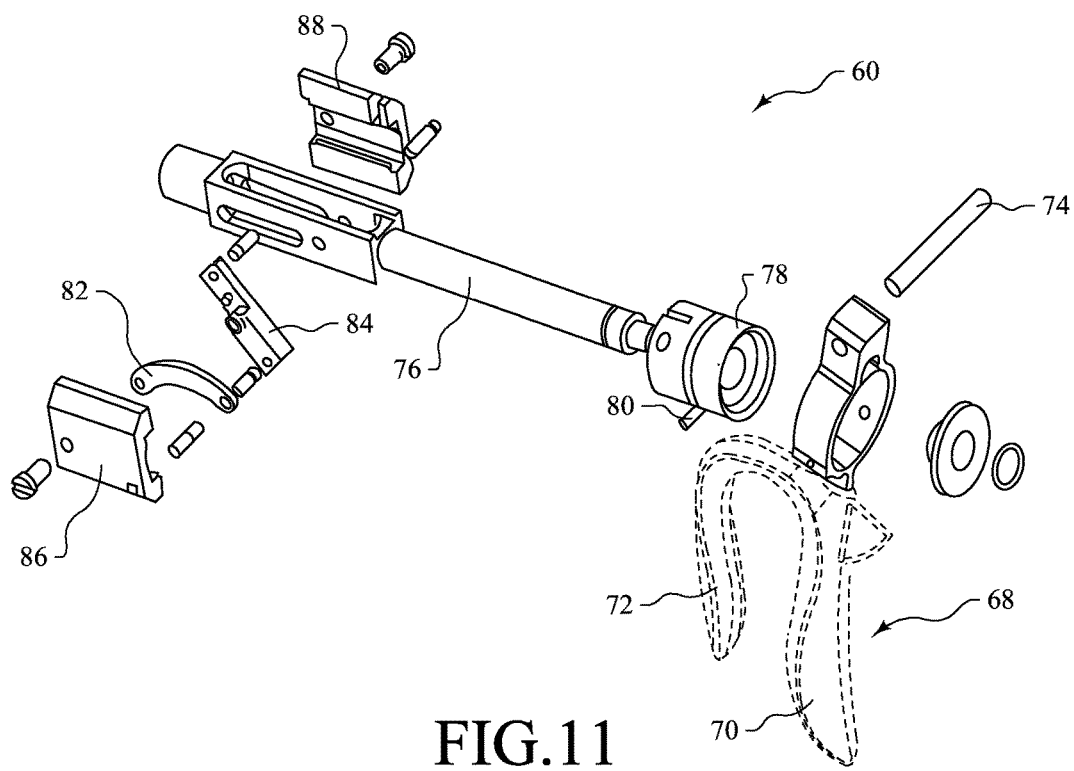
FIG. 11 is an exploded perspective view of the control end and triggering mechanism of a suturing device.
Figure 12:
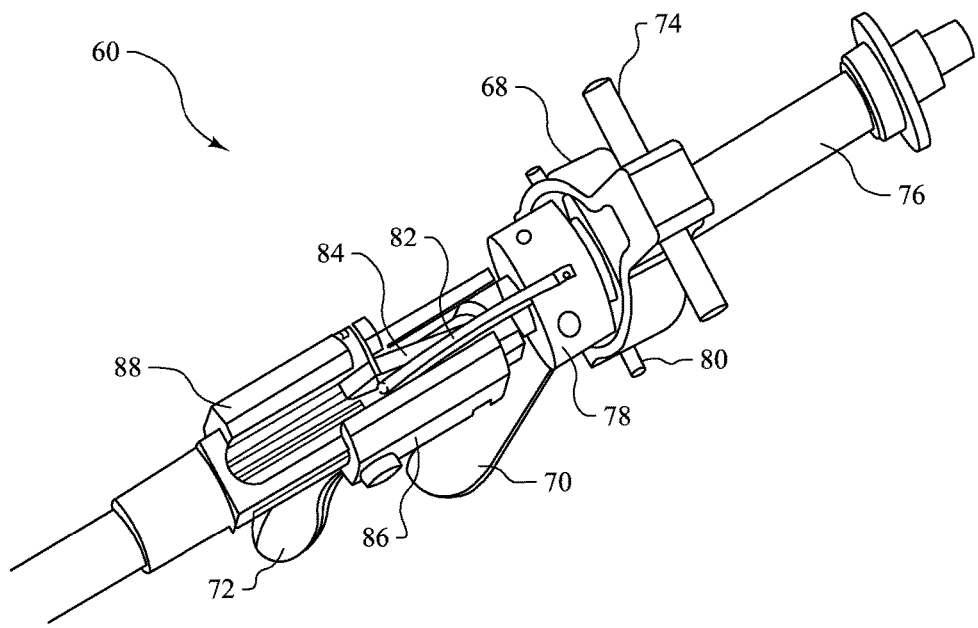
FIG. 12 is a partial perspective view of the control end and triggering mechanism of a suturing device.

Referring now to FIGS. 10-14, one exemplary triggering mechanism 60 that may be employed to operate the drive mechanism 50 of FIGS. 2-9 is provided. As shown, the triggering mechanism 60 may be disposed within a housing 62 provided at the control end 24 of the suturing device 20 and configured to interface with the first and second needles 38, 40 via the elongate member 22 and the drive mechanism 50 disposed therein. Furthermore, one or more of the elongate member 22 and the drive mechanism 50 therein may be rotatably coupled to the housing 62 via a rotating collar 64 which may be used to adjust the radial position of the firing aperture 32 relative to the control end 24. The housing 62 may further provide a grip 66 relative to which a trigger 68 of the triggering mechanism 60 may be pivotally anchored by an anchoring pin 70 and movable in one of two directions. For example, the trigger 68 may be configured to engage the drive mechanism 50 and advance the needles 38, 40 when pulled toward the grip 66, and disengage the drive mechanism 50 and retract the needles 38, 40 when pushed away from the grip 66. Correspondingly, as shown in FIG. 10, the trigger 68 may be provided with a proximal handle 72 for pulling the trigger 68 toward the grip 66, as well as a distal handle 74 for pushing the trigger 68 away from the grip 66.

Still referring to FIG. 10, the triggering mechanism 60 may further include a yoke 76 that is rigidly and axially coupled to the elongate member 22 and rotatably disposed within the housing 62. The triggering mechanism 60 may additionally include a drive collar 78 that is axially movable relative to the yoke 76 and pivotally anchored to the trigger 68 via a lynch pin 80. Furthermore, as shown in FIGS. 10-14, the interface between the drive collar 78 and the lynch pin 80 may be configured such that the drive collar 78 is pivotally anchored to the trigger 68 irrespective of the rotational position of the drive collar 78 relative to the trigger 68 and the housing 62. The drive collar 78 may additionally be linked to the yoke 76 via a collar link 82 and a reversing lever 84 such that the rotational position of the drive collar 78 follows the rotational position of the yoke 76. As shown in FIGS. 10-14, for example, the proximal end of the collar link 82 may be pivotally as well as radially coupled to the drive collar 78, and the distal end of the collar link 82 may be pivotally and radially coupled to the yoke 76.

The triggering mechanism 60 of FIGS. 10-14 may further provide means for translating a single action received by a user at the control end 24 of the suturing device 20 into two or more simultaneous but opposing actions effectuated at the working end 26. For example, the distal end of the collar link 82 may be coupled to the yoke 76 via a reversing lever 84, the substantial center of which may be pivotally anchored to the yoke 76. In particular, a first end of the reversing lever 84 may be pivotally coupled to a first sliding block 86 that is rigidly coupled to the first drive link 52 but slidably movable relative to the yoke 76. Correspondingly, a second end of the reversing lever 84, opposite the first end, may be pivotally coupled to a second sliding block 88 that is rigidly coupled to the second drive link 54 but also slidably movable relative to the yoke 76. In addition, the collar link 82 may be pivotally coupled proximate and biased to one of the first and second ends of the reversing lever 84 such that, for example, pushing the collar link 82 in a distal direction rotates the reversing lever 84 relative to the yoke 76 in a first direction, and pulling the collar link 82 in a proximal direction rotates the reversing lever 84 in a second direction opposite to the first direction.

Figure 13:
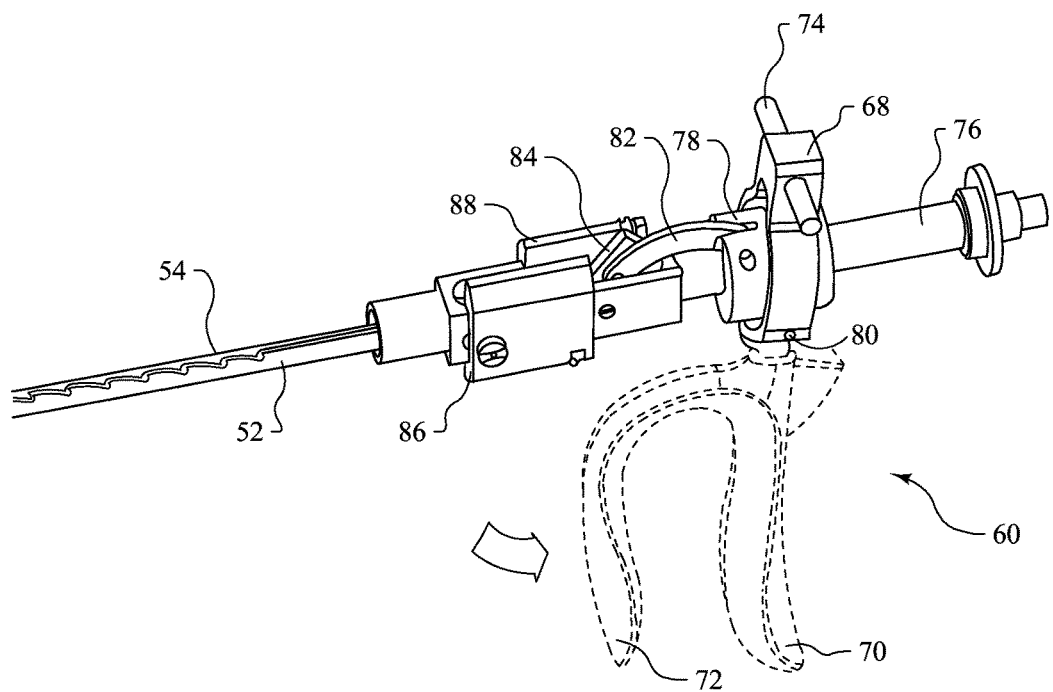
FIG. 13 is a partial perspective view of the control end and triggering mechanism of a suturing device in the engaged state.
Figure 14:
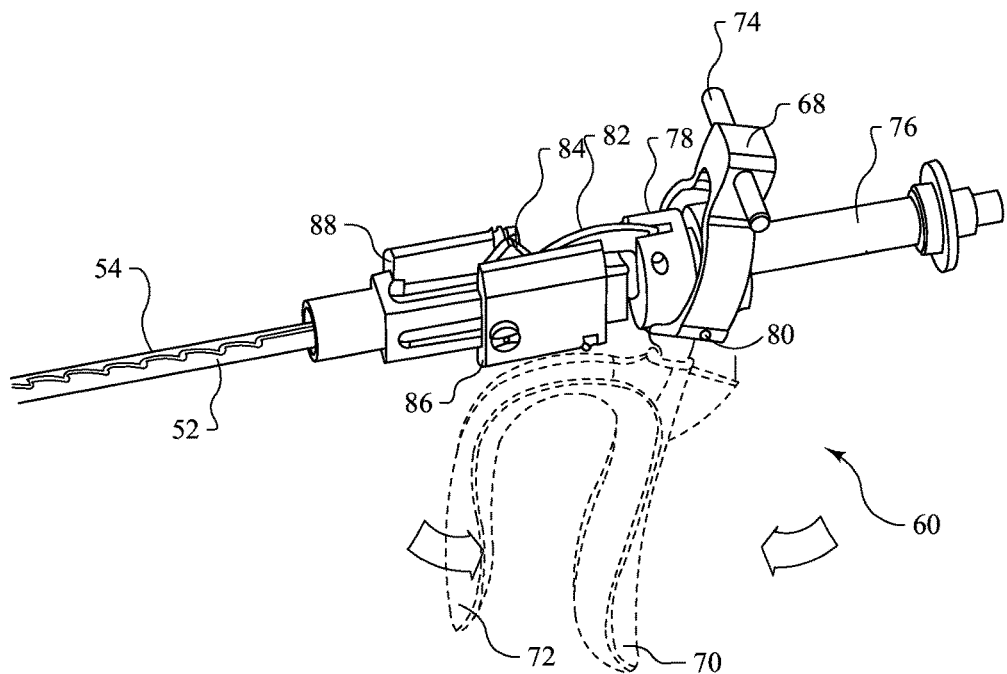
FIG. 14 is a partial perspective view of the control end and triggering mechanism of a suturing device in the disengaged state.

As illustrated in FIGS. 13 and 14, for example, the collar link 82 may be coupled proximate to the second end of the reversing lever 84 which may further be coupled to the second sliding block 88. In this particular arrangement, when the trigger 68 is moved toward the grip 66 as indicated by the arrow in FIG. 13, the drive collar 78 and the collar link 82 may be pulled toward the control end 24 of the suturing device 20, thereby causing the reversing lever 84 to pivot in the manner shown and slidably urge the first sliding block 86, as well as the first drive link 52 coupled thereto, in the distal direction while simultaneously urging the second sliding block 88, as well as the second drive link 54 coupled thereto, in the proximal direction. Moving the trigger 68 in the manner shown in FIG. 13 may thus cause the drive mechanism 50 to engage and actuate the first and second needles 38, 40. Conversely, when the trigger 68 is moved away from the grip 66 as indicated by the arrow in FIG. 14, the drive collar 78 and the collar link 82 may be pushed toward the working end 26 of the suturing device 20, thereby causing the reversing lever 84 to pivot in the opposite direction and slidably urge the first sliding block 86, as well as the first drive link 52, in the proximal direction while simultaneously urging the second sliding block 88, as well as the second drive link 54, in the distal direction. Correspondingly, moving the trigger 68 in the manner shown in FIG. 14 may cause the drive mechanism 50 to disengage and retract the first and second needles 38, 40.

Figure 17:
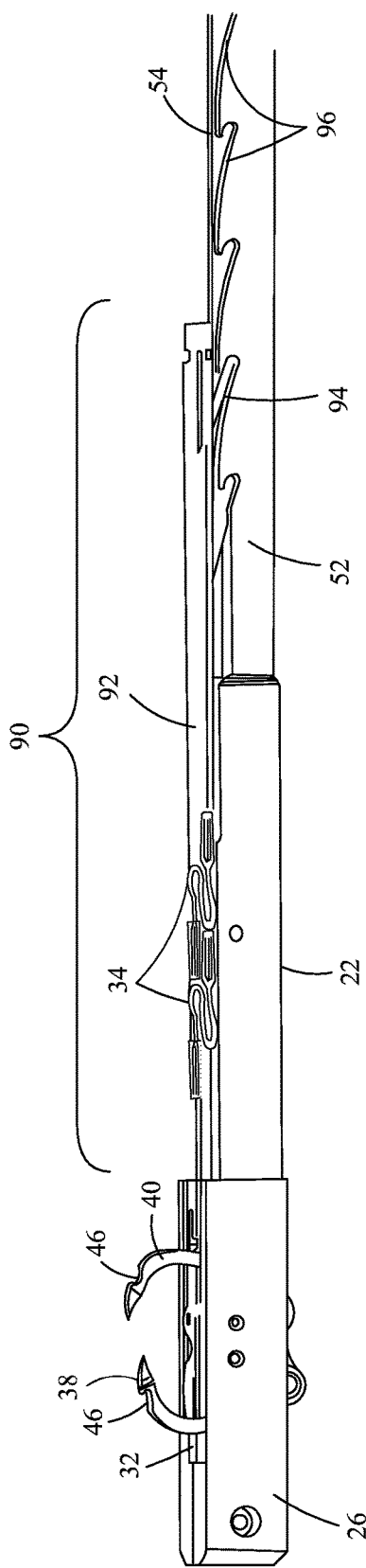
FIG. 17 is a partial side plan view of the working end, elongate member and autoloading mechanism of a suturing device during engagement.
Figure 18:
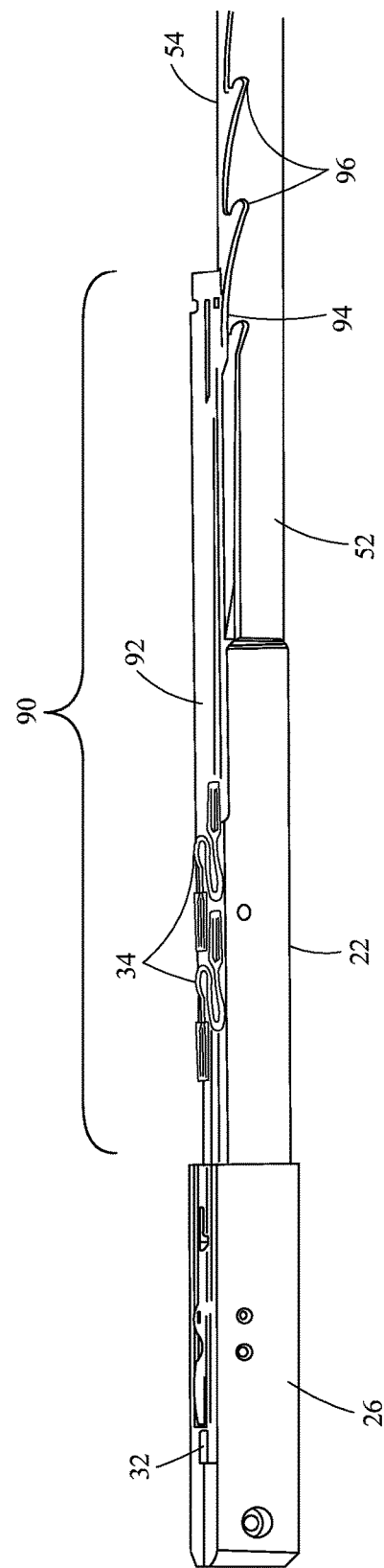
FIG. 18 is a partial side plan view of the working end, elongate member and autoloading mechanism of a suturing device during disengagement.

Turning to FIGS. 15-27, the suturing device 20 may additionally include an autoloading mechanism 90 for successively feeding and automatically loading one of a plurality of sutures 34 into position relative to the firing aperture 32 for deployment. As shown in FIGS. 15 and 16, for example, a plurality of successively deployable sutures 34, in the form of replaceable suture cartridges, suture ribbons, suture strings, or the like, may be removably inserted along guides or tracks 36 disposed within the elongate member 22. The autoloading mechanism 90 may provide a pusher member 92 that is also slidably disposed along the tracks 36 and configured to successively or incrementally urge the sutures 34 toward the firing aperture 32 for deployment. As shown in FIGS. 17 and 18 for example, the pusher member 92 may include at least one flexible pusher tab 94 extending therefrom that is biased so as to unidirectionally interface with one or more catches 96 that are disposed along one of the first and second drive links 52, 54 of the drive mechanism 50. Moreover, the pusher tab 94 and the catches 96 may be configured such that the pusher member 92 urges the sutures 34 toward the firing aperture 32 during engagement of the drive mechanism 50 or advancement of the needles 38, 40.

As shown in the particular arrangement of FIGS. 17 and 18, for example, the pusher member 92 may be configured such that at least one pusher tab 94 engages with one of the catches 96 disposed on the first drive link 52, and thereby moves the pusher member 92 in direct correspondence with the first drive link 52. In this configuration, as shown in FIG. 17, the pusher member 92 may be urged to push the sutures 34 toward the firing aperture 32 while the first and second drive links 52, 54 are being engaged and while the first and second needles 38, 40 are being advanced. Furthermore, in this particular configuration, when the drive mechanism 50 is being disengaged and when the needles 38, 40 are being retracted, as shown in FIG. 18, the catches 96 of the first drive link 52 may be free to return and move away from the working end 26 while the pusher member 92 remains stationary relative to the sutures 34 and the firing aperture 32. Moreover, the pusher member 92 may include support members 97 as shown in FIG. 15 configured to essentially wedge the pusher member 92 within the guides or tracks 36 of the elongate member 22 and provide the pusher member 92 at least some resistance against longitudinal movement therealong. The positioning of the catches 96 along the first drive link 52 may be spaced according to the distance allotted for each suture 34. In addition, the number of catches 96 and the freedom of travel of the pusher member 92 may also be configured so as to sufficiently adapt to the changing length of the string of available sutures 34 which incrementally shortens after each deployment.

While the embodiments shown may disclose interactions between the pusher tab 94 and catches 96 provided on the first drive link 52, the pusher tab 94 may alternatively interact with catches 96 disposed on the second drive link 54 or any combination of the first and second drive links 52, 54. In still further alternative embodiments, the pusher member 92 may be configured to interact with the drive mechanism 50 in other manners not shown, so long as the drive mechanism 50 is able to engage the pusher member 92 to timely and appropriately urge one or more sutures 34 toward the firing aperture 32 for deployment upon deployment of a prior suture 34.

Figure 19:
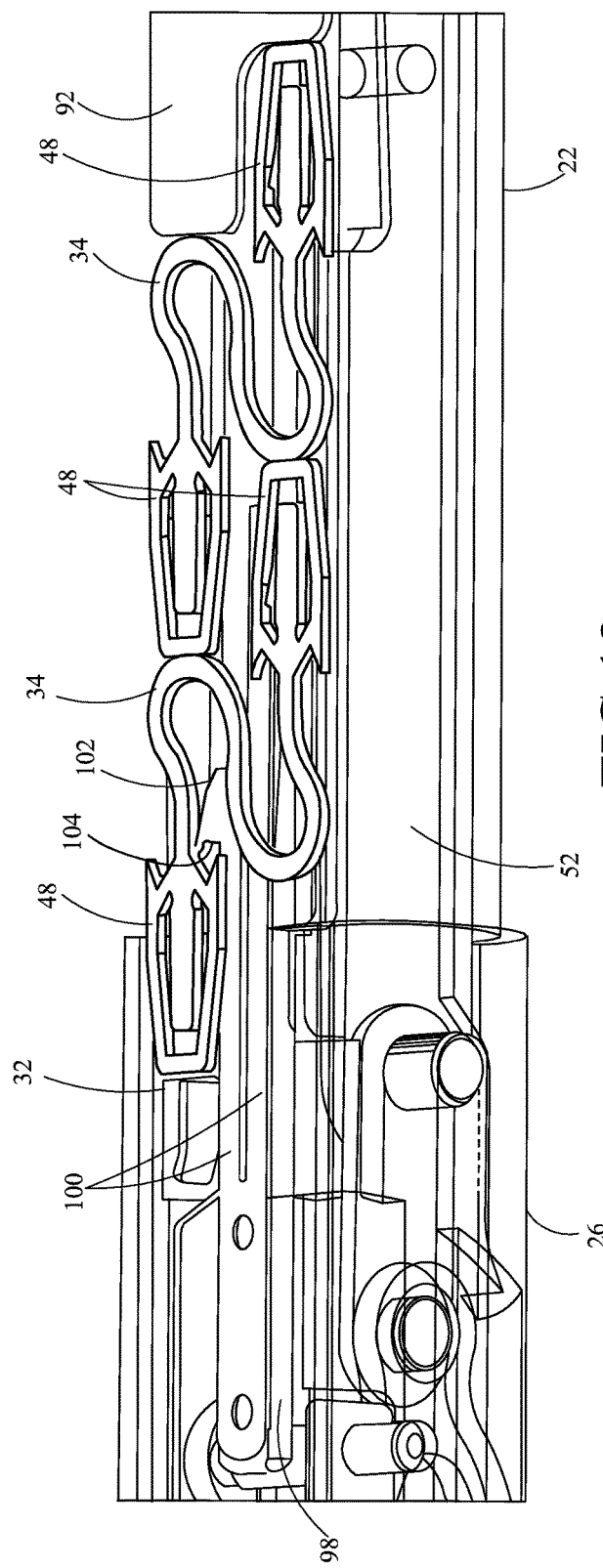
FIG. 19 is a partial perspective view of the autoloading mechanism of a suturing device.

While the pusher member 92 and the catches 96 of the first drive link 52 of FIGS. 15-18 may aid in urging the string of sutures 34 toward the working end 26 for deployment, the extent to which the sutures 34 are pushed may be limited so as not to obstruct the firing aperture 32 through which the first and second needles 38, 40 will need to extend in order to deploy a prior suture 34. Accordingly, the autoloading mechanism 90, as shown in FIGS. 19-27, may further include a shuttle 98 configured to retrieve the next suture 34 in line for deployment and position the suture 34 over the firing aperture 32 in alignment with the needles 38, 40 upon full deployment and release of a prior suture 34. As shown in FIG. 19, the shuttle 98 may be slidably disposed along the elongate member 22 and beneath the string of sutures 34 to be deployed. Moreover, the shuttle 98 may be movably disposed in communication between the working end 26 and the elongate member 22 such that the distance of travel of the shuttle 98 extends between at least the firing aperture 32 and the next suture 34 in line for deployment.

Figure 20:
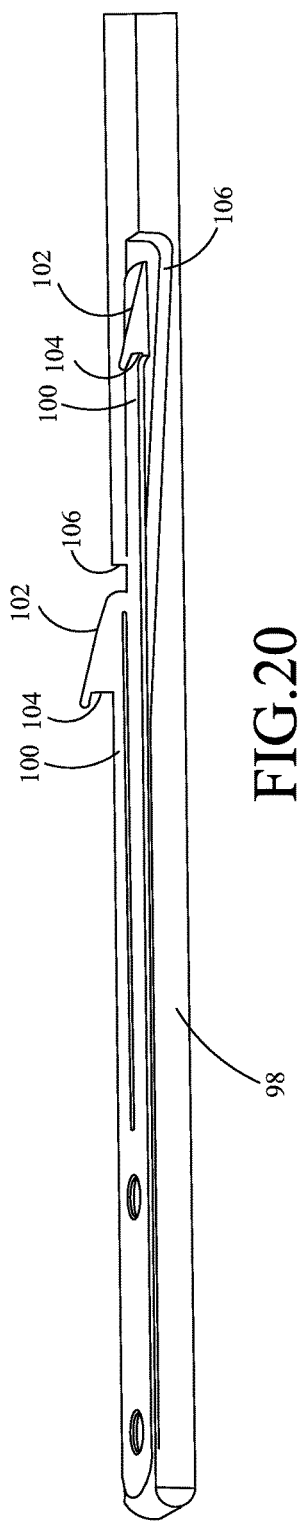
FIG. 20 is a partial perspective view of the shuttle of the autoloading mechanism of a suturing device.

As shown in FIG. 20, the shuttle 98 may further include one or more suture pawls 100 for engaging with a suture 34 prior to deployment. More specifically, the suture pawls 100 may be configured such that the shuttle 98 is engaging when traveling in one direction but non-engaging when traveling in the opposite direction. In the embodiments of FIGS. 19 and 20, for example, each of the suture pawls 100 may include a ramped edge 102 facing the proximal direction and a hooked edge 104 facing the opposite, distal direction. In addition, each of the suture pawls 100 may be formed of a partially flexible material and allowed to deflect within recesses 106 formed within the shuttle 98. In such a way, the deflectable ramped edges 102 may enable the suture pawls 100 and the shuttle 98 to proximally travel from the firing aperture 32 to beneath the sutures 34 without substantial obstruction and without adversely affecting the position of the sutures 34. Once the shuttle 98 is in the appropriate position beneath the next suture 34 in line for deployment, as shown in FIG. 19, the hooked edges 104 may be upright and in position to slidably engage with the suture 34. As the shuttle 98 returns toward the working end 26, the hooked edges 104 of the suture pawls 100 may distally slide the next suture 34 onto the firing aperture 32. Moreover, the suture 34 may be positioned such that any needle guides 48 thereof are appropriately aligned with one or more corresponding needles 38, 40.

Turning to FIG. 21, the autoloading mechanism 90 may further interface with the drive mechanism 50 to at least cause the shuttle 98 of FIGS. 19 and 20 to move between the firing aperture 32 and the string of suture 34. As shown, the autoloading mechanism 90 may include a shuttle pawl 108 that is generally disposed beneath the shuttle 98 and coupled to one of the first and second drive links 52, 54 of the drive mechanism 50. While other configurations are possible, in the particular embodiments shown, for example, the shuttle pawl 108 may be coupled to the first drive link 52. Moreover, the shuttle pawl 108 may include a ramped edge 110 facing the distal direction that is configured such that the first drive link 52 and the shuttle pawl 108 are freely movable in the distal direction relative to the shuttle 98 without substantial obstruction or interference therewith, such as during advancement of the needles 38, 40. As illustrated, the shuttle pawl 108 may be formed of a flexible material that can be deflected within a recess 112 of the first drive link 52. The shuttle pawl 108 may additionally include a hooked edge 114 facing the proximal direction that is configured such that the shuttle pawl 108 pulls the shuttle 98 with the first drive link 52 when the first drive link 52 moves in the proximal direction, such as during retraction of the needles 38, 40.

As shown more particularly in FIG. 22, during engagement of the drive mechanism 50 or during advancement of the first and second needles 38, 40, the first drive link 52 along with the shuttle pawl 108 may be distally pushed toward the working end 26 of the suturing device 20 in the manner shown. As the shuttle pawl 108 approaches the shuttle 98, the ramped edge 110 thereof may enable the shuttle pawl 108 to deflect into the recess 112 of the first drive link 52, and further, enable the shuttle pawl 108 to glide under the shuttle 98 without altering the position of the shuttle 98 relative to the sutures 34. Each of the first drive link 52 and the shuttle pawl 108 may progress in such a way at least until the hooked edge 114 of the shuttle pawl 108 reaches and interfaces with the distal end of the shuttle 98. Both the first drive link 52 and the shuttle pawl 98 may be sized and configured such that the hooked edge 114 interfaces with distal end of the shuttle 98 once the needles 38, 40 are in the fully extended positions and ready to engage and deploy the prior suture 34 as shown in FIG. 21. Correspondingly, during disengagement of the drive mechanism 50 or during retraction of the needles 38, 40, the first drive link 52 along with the shuttle pawl 108 and the engaged shuttle 98 may be proximally pulled toward the string of sutures 34 so as to retrieve the next suture 34 in line for subsequent deployment.

Figure 23:
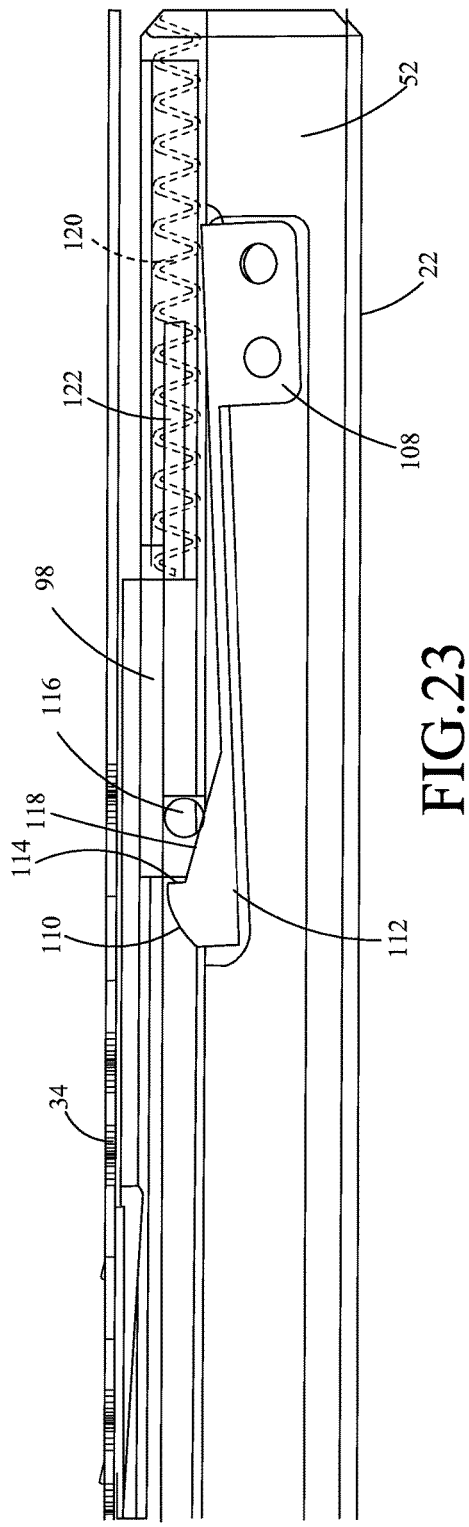
FIG. 23 is a partial side plan view of the autoloading mechanism of a suturing device during disengagement.

Once the shuttle 98 is sufficiently pulled beneath the next suture 34 to be deployed, the shuttle pawl 108 may be configured to automatically release the shuttle 98 so as to enable the shuttle 98 to return to the working end 26 and send the retrieved suture 34 therewith to the appropriate position over the firing aperture 32. As shown in FIG. 23, for example, the autoloading mechanism 90 may thus provide a declutch feature, such as a declutch pin 116, or the like, configured to release the shuttle pawl 108, or release the shuttle 98 from the first drive link 52, once the shuttle 98 is appropriately positioned beneath the next suture 34 in line for deployment. For example, the declutch pin 116 may be coupled within the elongate member 22 and fixedly positioned relative to the shuttle pawl 108 such that, as the shuttle pawl 108 proximally passes thereby, the shuttle pawl 108 is caused to deflect within the recess 112 of the first drive link 52 and allow the shuttle 98 to return to the working end 26. Furthermore, the shuttle pawl 108 may further provide a ramped interface 118 which proximally precedes the hooked edge 114 and is configured to sufficiently deflect and release the shuttle pawl 108 from the shuttle 98 at the appropriate moment, for instance, when the suture pawls 100 of the shuttle 98 are ready to engage with the next suture 34 in line for deployment.

Still referring to FIG. 23, once the shuttle pawl 108 is fully deflected, the shuttle 98 and the retrieved suture 34 may be sent to the firing aperture 32 by a bias mechanism 120 configured to continuously bias or urge the shuttle 98 toward the working end 26. As shown, the bias mechanism 120 may employ a compression spring, or the like, that is longitudinally disposed within the elongate member 22 and configured to distally push the shuttle 98 away therefrom. In further modifications, the proximal end of the shuttle 98 may further provide a centering rod 122 longitudinally extending therefrom configured to interface with the compression spring of the bias mechanism 120 and maintain centering of the shuttle 98 relative to the elongate member 22 and the firing aperture 32. Similarly, other bias mechanisms 120 may be employed to achieve comparable results so long as the biasing force applied upon the shuttle 98 in the distal direction does not exceed the force exerted thereon in the proximal direction by the shuttle pawl 108 and the first drive link 52.

Figure 24:
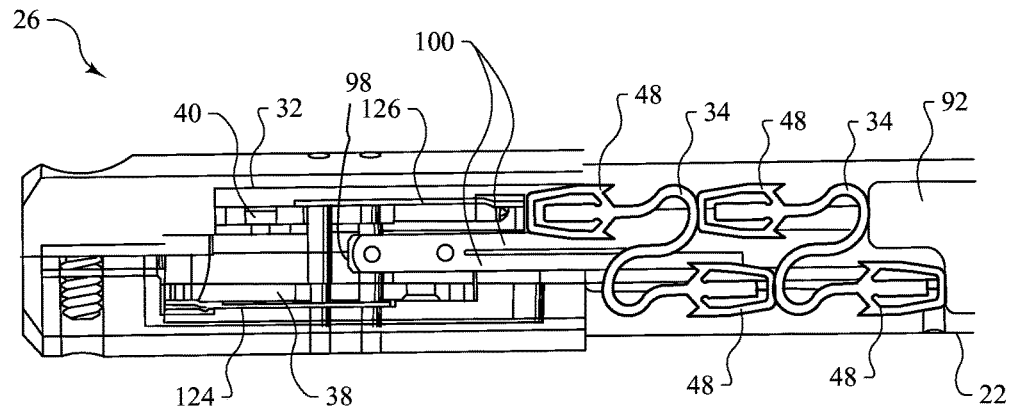
FIG. 24 is a partial top plan view of the working end and autoloading mechanism of a suturing device retrieving a suture for deployment.
Figure 25:
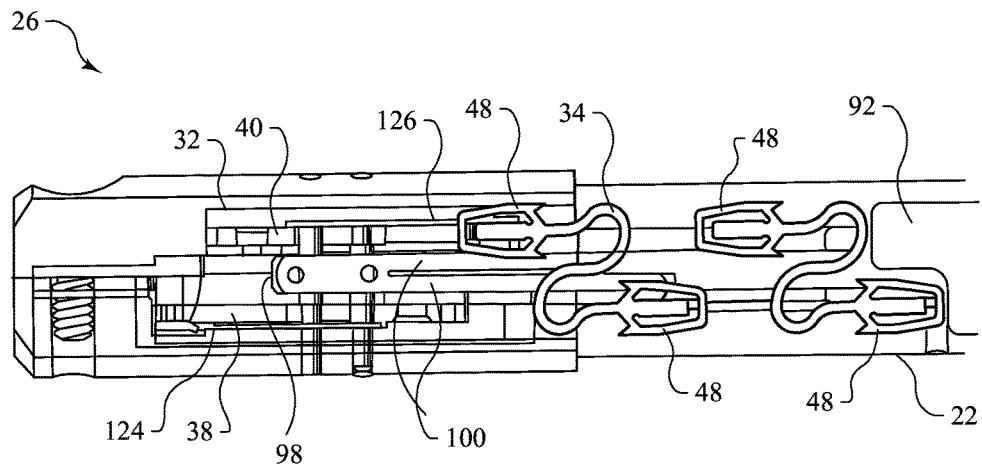
FIG. 25 is a partial top plan view of the working end and autoloading mechanism of a suturing device sending a retrieved suture for deployment.
Figure 26:
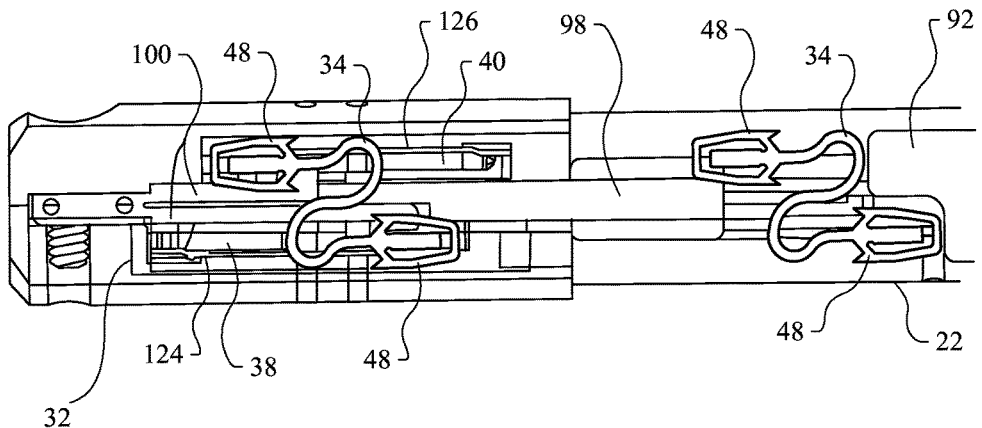
FIG. 26 is a partial top plan view of the working end and autoloading mechanism of a suturing device positioning a retrieved suture for deployment.

Turning now to FIGS. 24-26, one exemplary embodiment of the autoloading mechanism 90 is shown as it progressively retrieves the next suture 34 in line for deployment, and appropriately positions the suture 34 upon the firing aperture 32. More specifically, as shown in FIG. 24, the shuttle 98 as well as the suture pawls 100 are proximally pulled toward the string of sutures 34 as the drive mechanism 50 is disengaged or as the needles 38, 40 are retracted. As illustrated, the shuttle 98 is proximally pulled until at least the suture pawls 100 are in position to slidably engage respective sections of the suture 34. For instance, each suture pawl 100 may be configured to engage an exterior of a needle guide 48 of the suture 34, an interior of a needle guide 48, or any other portion of the suture 34 that is suitable for carrying the suture 34 to the firing aperture 32. Once released, the shuttle 98 and the suture pawls 100, as well as the next suture 34 to be deployed, may be distally pushed toward the firing aperture 32 while leaving the remaining string of sutures 34 behind, as shown for instance in FIG. 25. Furthermore, as shown in FIG. 26, the shuttle 98 may continue carrying the suture 34 toward the firing aperture 32 until each of the needle guides 48 of the suture 34 is appropriately aligned to be engaged by the corresponding needle 38, 40.

Figure 27:
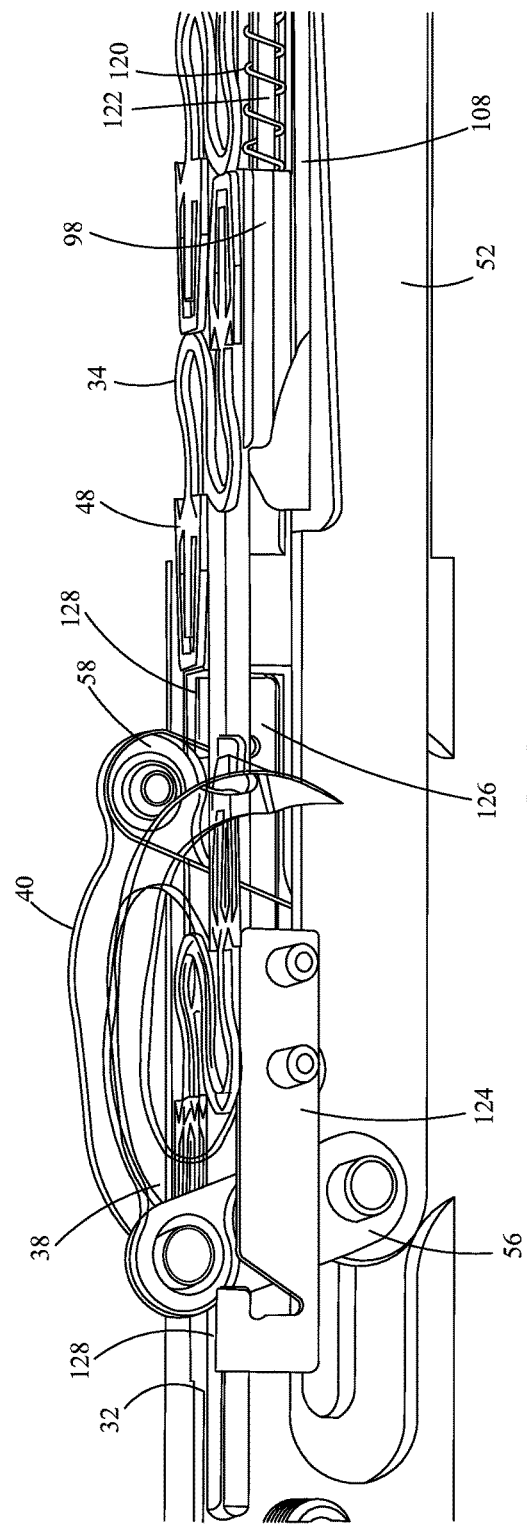
FIG. 27 is a partial perspective view of the working end, first and second needles and autoloading mechanism of a suturing device during engagement.

In addition, as shown in FIG. 27, the autoloading mechanism 90 may also provide one or more release mechanisms 124, 126 for completely deploying or releasing an engaged suture 34 from the first and second needles 38, 40 during retraction thereof. For example, each release mechanism 124, 126 may employ a blade or a cutting edge 128 that is longitudinally disposed within the firing aperture 32 and fixedly positioned proximate the retracted position of the corresponding needle 38, 40 such that, as the needle 38, 40 is retracted back into the firing aperture 32 and restored to its fully retracted position, the movement thereof relative to the cutting edge 124 causes the needle guide 48 of the suture 34 to be cut and released therefrom. In the particular embodiment of FIG. 24, for instance, a first release mechanism 124 is fixedly disposed within the firing aperture 32 and proximate the first needle 38, while the second release mechanism 126 is fixedly disposed within the firing aperture 32 and proximate the second needle 40. Moreover, in each release mechanism 124, 126, the cutting edge 128 may be specifically positioned such that an engaged suture 34 is cut and completely released by the time the corresponding needle 38, 40 returns to its retracted position. While only cutting edges 128 are shown, the release mechanisms 124, 126 may alternatively employ hooks, pawls, ramped edges, or any suitable device capable of releasing the suture 34 from the needles 38, 40 or hooks 46 thereof either by cutting or unlatching the suture 34 therefrom.

Figure 28:
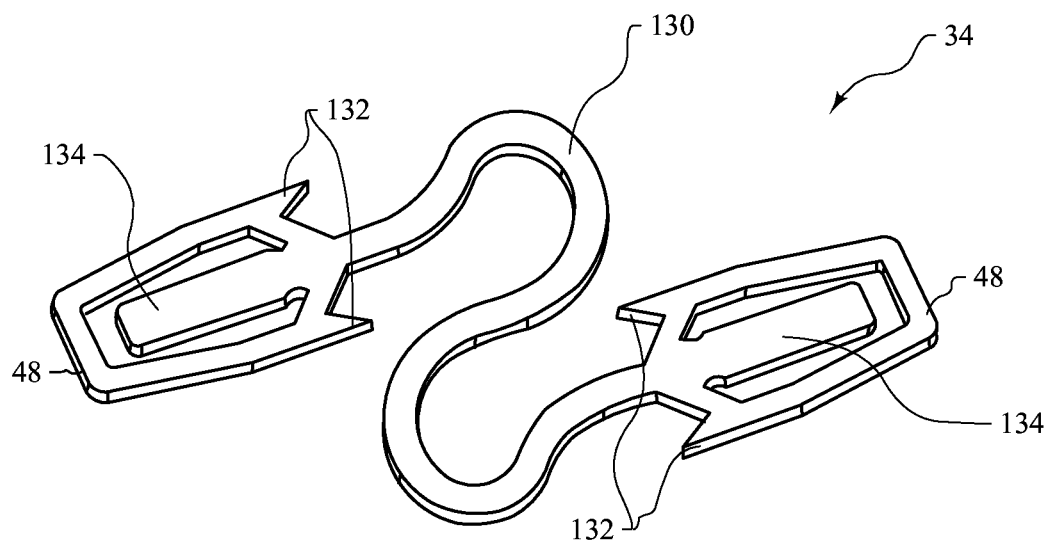
FIG. 28 is a perspective view of one exemplary embodiment of a fastener having constriction elements constructed in accordance with the teachings of the present disclosure.
Figure 29:
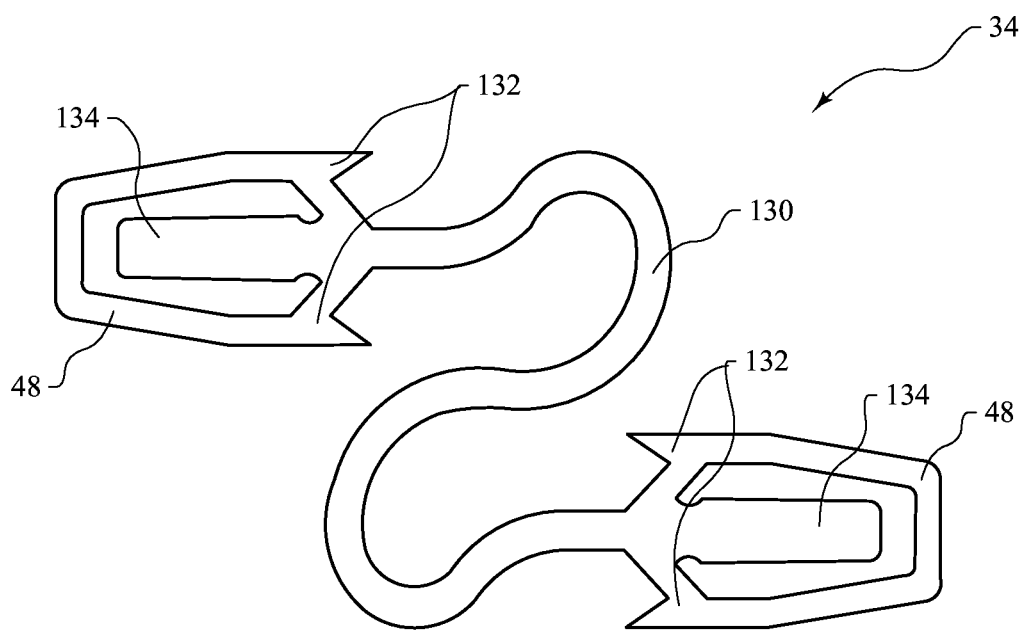
FIG. 29 is a top plan view of a fastener having constriction elements.

Referring now to FIGS. 28 and 29, one exemplary embodiment of a tissue fastener or suture 34 constructed in accordance with the teachings of the present disclosure is provided. As shown, the suture 34 may generally comprise an elongated filament 130 extending between a first end and a second end, and at least one needle guide 48 disposed at one or more of the first and second ends of the elongated filament 130. The suture 34 may be unitarily formed of a material that is sufficiently flexible and compliant so as to be appropriately deployable by a suturing device 20, while also providing sufficient resilience or rigidity to maintain closure between tissue and/or prosthetic material upon deployment. Additionally, the elongated filament 130 may be formed with one or more planar curves, such as the S-shaped curve shown, or the like, so as to provide for a more compact overall package and to increase the number of sutures 34 that can be made available for deployment, for example, along the elongated member 22 of a given suturing device 20. Furthermore, the planar curves of the elongated filament 130 may be configured according to the anticipated geometry of the suture 34 once deployed and installed within tissue and/or prosthetic material.

Still referring to the sutures 34 of FIGS. 28 and 29, each needle guide 48 may be sufficiently sized and configured to be engaged by, for example, one of the needles 38, 40 of the suturing device 20 of FIG. 1-27, or one the needle hooks 46 thereof, while also being sufficiently easily released from the needles 38, 40, for example, via any of the release mechanisms 124, 126 provided in FIGS. 24-27. The needle guides 48 may further be shaped, for example, with a relatively tapered tip that is configured to facilitate advancement thereof through tissue and/or prosthetic material during deployment, as well as resist retraction thereof to promote a secure closure. For example, the needle guides 48 may be shaped in the substantial form of an oval, an ellipse, a circle, a semi-circle, a triangle, a polygon, or the like. As shown, each needle guide 48 may additionally include one or more retention elements 132 that are also configured to facilitate advancement thereof through sections of tissue and/or prosthetic material, and further aid in resisting retraction thereof once deployed. The retention elements 132 may be shaped in the form of a tine, a fin, a canted element, or any design sufficiently capable resisting retraction through tissue and/or prosthetic material.

Each of the needle guides 48 in FIGS. 28 and 29 may further be provided with one or more constriction elements 134 configured to further secure an engagement between the needle guide 48 and a corresponding needle 38, 40 or needle hook 46 thereof. More specifically, the constriction element 134 may be disposed within the needle guide 48 in a manner configured to at least partially bias or constrict the needle guide 48 against one of the needles 38, 40 received therethrough. As shown in FIGS. 28 and 29, for example, the constriction element 134 may take the form of a tab, flap, or the like, that is disposed within the needle guide 48 and extending toward the tapered end of the needle guide 48 or extending toward any other the portion of the needle guide 48 that is anticipated to be engaged by a needle hook 46. Moreover, the constriction elements 134 may be formed of a material that is sufficiently flexible and compliant so as to receive a needle 38, 40 therethrough, but also formed of a material with sufficient resilience and rigidity so as to bias the needle guide 48 against the needle 38, 40 and needle hook 46.

Figure 30:
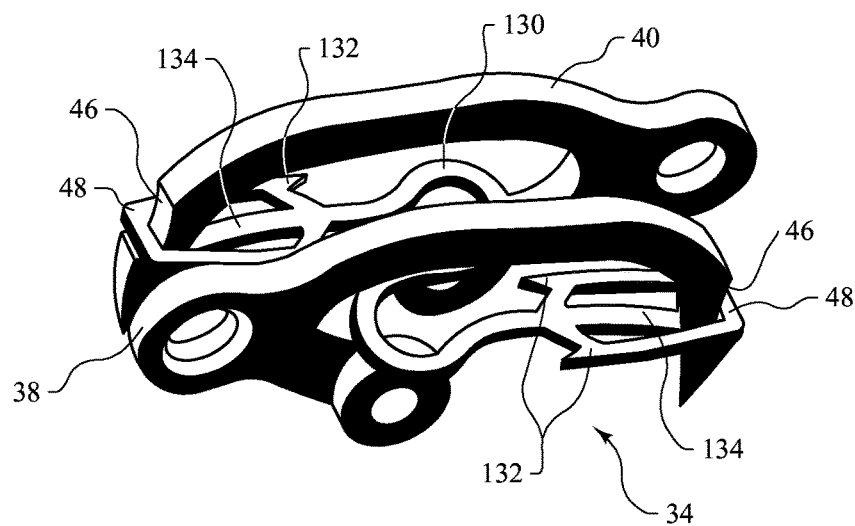
FIG. 30 is a partial perspective view of a fastener with constriction elements as engaged by first and second needles of a suturing device.
Figure 31:
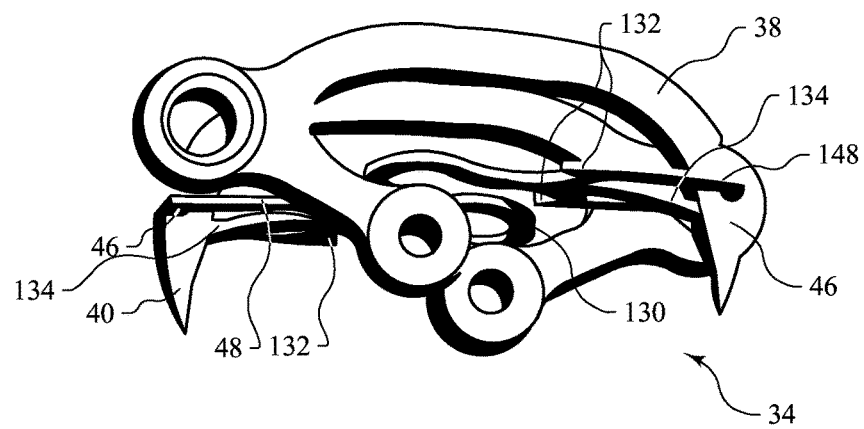
FIG. 31 is a partial perspective view of a fastener with constriction elements as engaged by first and second needles of a suturing device.
Figure 32:
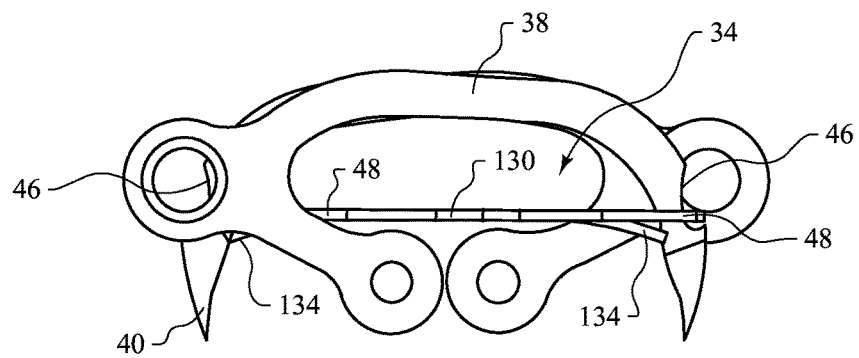
FIG. 32 is a partial perspective view of a fastener with constriction elements as engaged by first and second needles of a suturing device.

Turning to FIGS. 30-32, one exemplary interaction between the suture 34 of FIGS. 28 and 29 and a given set of needles 38, 40 and respective needle hooks 46 is provided. As shown, once the first and second needles 38, 40 are advanced into the fully extended positions and received through the respective needle guides 48, the constriction elements 134 are caused to bend, thereby pushing or exerting an outward force against the inner edge of the needles 38, 40. This outward pushing force exerted by the constriction element 134 may effectively exert a substantially equal and opposite inward force on the tapered end of the needle guide 48, thereby biasing the needle guide 48 into the needle hook 46 of the respective needle 38, 40. Thus, the constriction elements 134 of the sutures 34 may provide an otherwise absent constricting force on a received needle 38, 40, which may further serve to secure an engagement between the needle hook 46 and the needle guide 48 of the suture 34. While disclosed in the form of a tab or flap, the constriction elements 134 may be provided on the needle guides 48 in any one of variety of different forms, sizes and configurations. Alternatively, the constriction element 134 may be configured to substantially close the needle guide 48 except for one or more slots, apertures or other voids disposed toward the tapered end thereof in a manner which would effectively bias the needle guide 48 against a given needle hook 46. In still further alternatives, the constriction element 134 may be completely closed but penetrable by a needle 38, 40 in a manner which would effectively bias the needle guide 48 against the needle hook 46.

Figure 33:
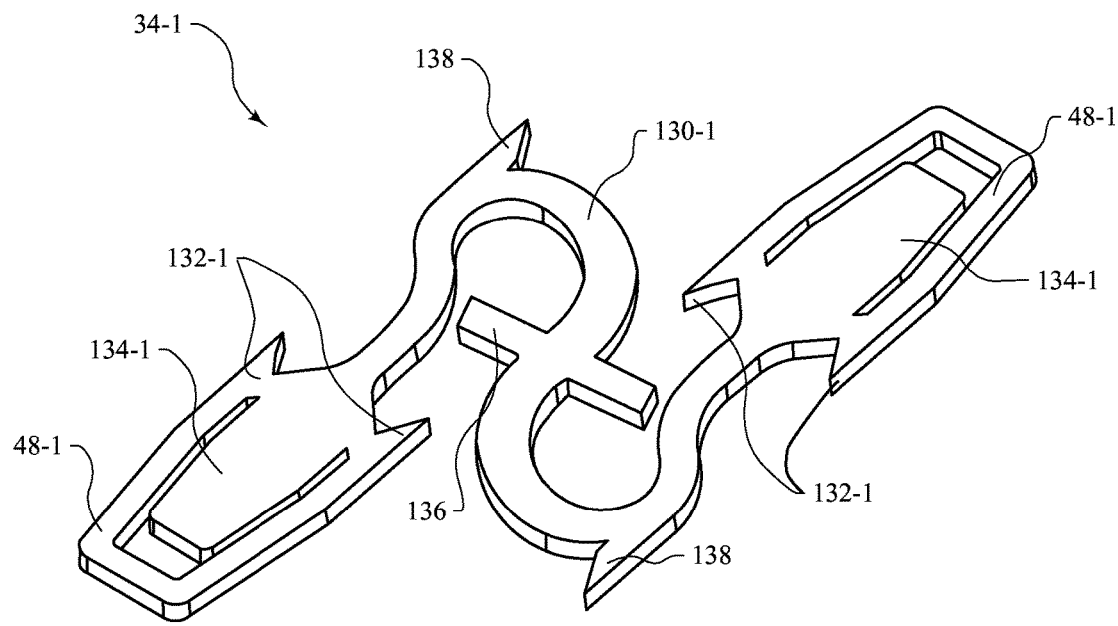
FIG. 33 is a perspective view of another exemplary embodiment of a fastener having constriction elements.
Figure 34:
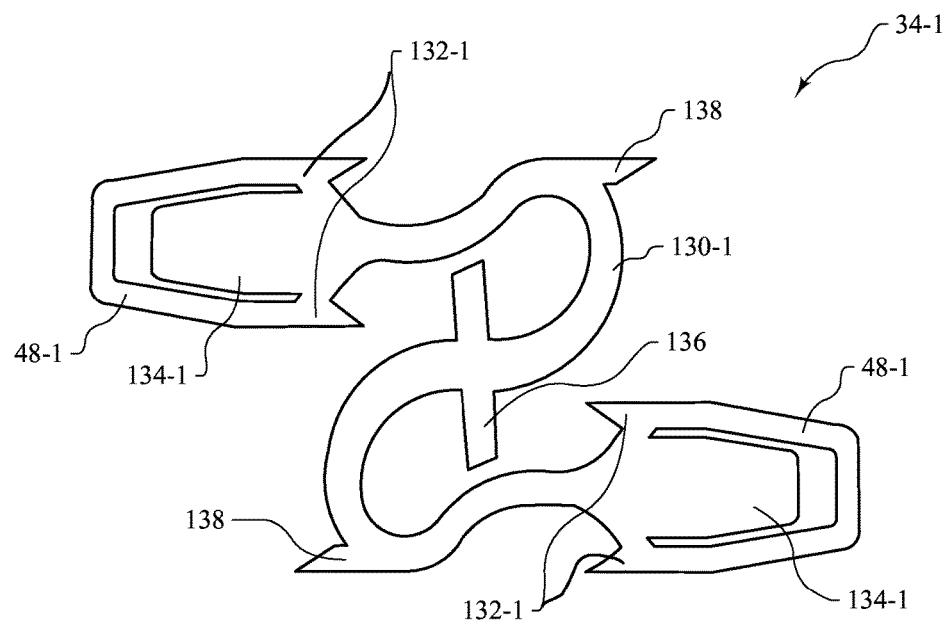
FIG. 34 is a top plan view of a fastener having constriction elements.

As shown in FIGS. 33 and 34, another exemplary embodiment of a tissue fastener or suture 34-1 that may be used in association with a suturing device 20 is provided. Similar to the suture 34 of FIGS. 28 and 29, the suture 34-1 shown may generally comprise an elongated filament 130-1 extending between a first end and a second end, and at least one needle guide 48-1 disposed at one or more of the first and second ends of the elongated filament 130-1. The suture 34-1 may be formed of a material that is sufficiently flexible and compliant so as to be appropriately deployable by a suturing device 20, while also providing sufficient resilience or rigidity to maintain closure between tissue and/or prosthetic material upon deployment. The elongated filament 130-1 of the suture 34-1 may further include a cross member 136 as well as filament guides 138 configured to stabilize the suture 34-1 as it is moved within the tracks 36 and along the elongate member 22 of a suturing device 20. For example, the cross member 136 may aid in increasing the structural integrity laterally across the suture 34-1 and reduce binding, while the filament guides 138 may be sized and configured to interface with the tracks 36 of the elongate member 22 of a suturing device 20 so as to provide the suture 34-1 with additional lateral support and maintain proper alignment thereof. Furthermore, any one or more of the cross member 136 and the filament guides 138 may be configured with retention features configured to aid in resisting retraction thereof once deployed into tissue and/or prosthetic material.

As in previous embodiments, the needle guides 48-1 of FIGS. 33 and 34 may be sufficiently sized and configured to be engaged by a needle 38, 40 of a suturing device 20, or one of the needle hooks 46 thereof, while also being sufficiently thin or easily released from the needles 38, 40, for example, via any of the release mechanisms 124, 126 provided in FIGS. 24-27. As shown, the needle guides 48-1 may be provided with a relatively tapered tip, as well as provided with one or more retention elements 132-1, configured to facilitate advancement thereof through tissue and/or prosthetic material during deployment, and resist retraction thereof to promote a secure closure. Each of the needle guides 48-1 in FIGS. 33 and 34 may be provided with constriction elements 134-1 which substantially conform to the shape of the needle guides 48-1 and serve to secure an engagement between the needle guide 48-1 and a corresponding needle 38, 40 or needle hook 46 thereof. Specifically, each constriction element 134-1 may be configured to increase the integrity or lateral rigidity of each needle guide 48-1 when a needle 38, 40 is not inserted therethrough, such as when the suture 34-1 is being moved along the tracks 36 of the elongate member 22 of a suturing device 20, but also configured to effectively reduce the lateral rigidity of each needle guide 48-1 when a needle 38, 40 is received therethrough, such as during advancement through tissue and/or prosthetic material. As shown in FIGS. 33 and 34, for example, the constriction elements 134-1, when in the non-deflected state, may substantially fill the width of the needle guides 48-1, and thereby provide lateral support thereacross. When in the deflected state, the constriction elements 134-1 may enable the needle guides 48-1 to substantially collapse and narrow so as to promote insertion or advancement thereof through a tissue, and the like. Furthermore, the constriction elements 134-1 may continue to provide lateral rigidity and support for the retention elements 132-1 once deployed and released into tissue and/or prosthetic material. For example, once the suture 34-1 is deployed and needle guides 48-1 are released, for instance cut, from the corresponding needles 38, 40, the constriction elements 134-1 may be configured to return to the non-deflected default state and thereby substantially prevent the retention elements 132-1 from collapsing and retracting from the tissue and/or prosthetic material.

Figure 35:
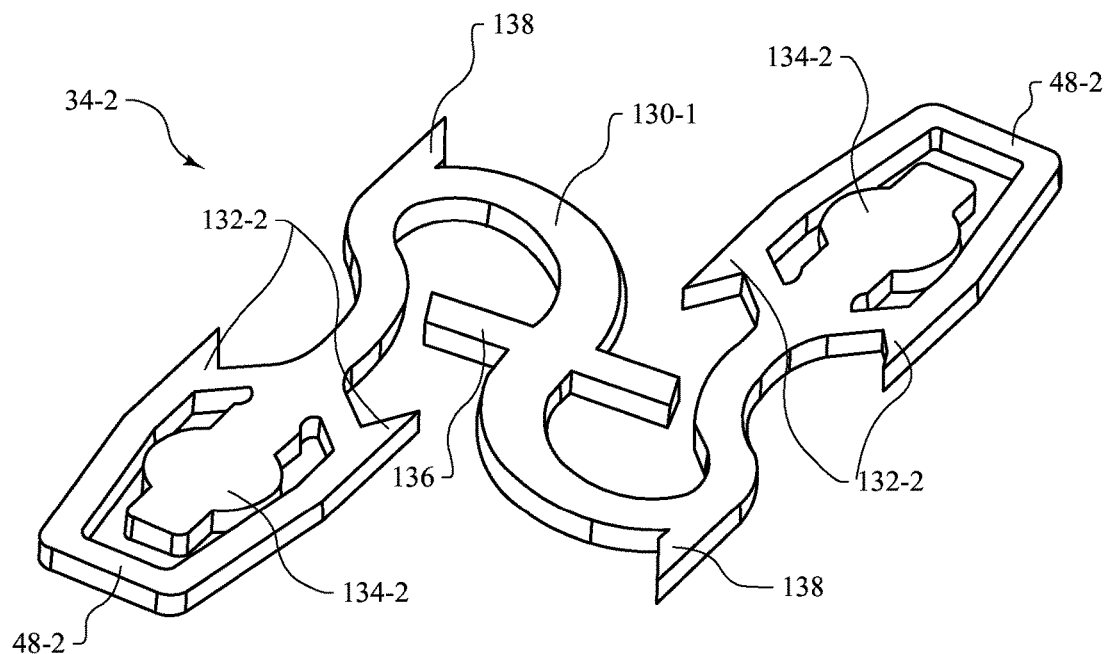
FIG. 35 is a perspective view of another exemplary embodiment of a fastener having constriction elements.
Figure 36:
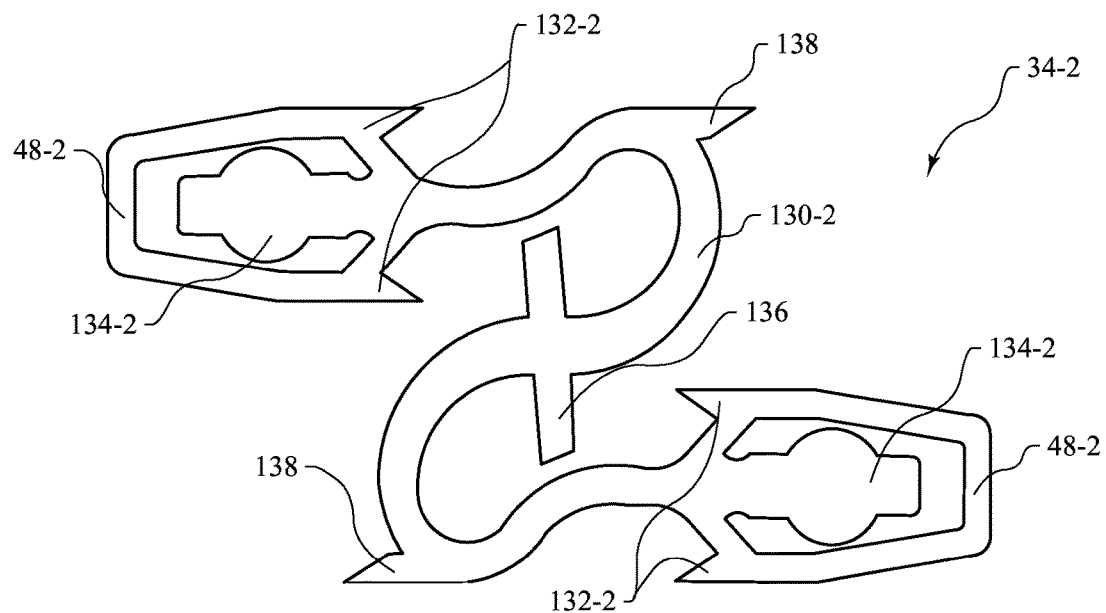
FIG. 36 is a top plan view of a fastener having constriction elements.

As additionally shown in FIGS. 35 and 36, another exemplary embodiment of a tissue fastener or suture 34-2 that may be used in association with a suturing device 20 is provided. As in previous embodiments, the suture 34-2 may generally comprise an elongated filament 130-2 extending between a first end and a second end, and at least one needle guide 48-2 disposed at one or more of the first and second ends of the elongated filament 130-2. The suture 34-2 may be formed of a material that is sufficiently flexible and compliant so as to be appropriately deployable by a suturing device 20, while also providing sufficient resilience or rigidity to maintain closure between tissue and/or prosthetic material upon deployment. The elongated filament 130-2 of the suture 34-2 may further include a cross member 136 as well as filament guides 138 configured to stabilize the suture 34-2 as it is moved within the tracks 36 and along the elongate member 22 of a suturing device 20. Additionally, any one or more of the cross member 136 and the filament guides 138 may be configured with retention features configured to aid in resisting retraction thereof once deployed into tissue and/or prosthetic material.

The needle guides 48-2 of FIGS. 35 and 36 may be sufficiently sized and configured to be engaged by a needle 38, 40 of a suturing device 20, or one of the needle hooks 46 thereof, while also being sufficiently thin or easily released from the needles 38, 40, for example, via any of the release mechanisms 124, 126 provided in FIGS. 24-27. The needle guides 48-2 may be provided with a relatively tapered tip, as well as provided with one or more retention elements 132-2, configured to facilitate advancement thereof through tissue and/or prosthetic material during deployment, and resist retraction thereof to promote a secure closure. Each of the needle guides 48-2 in FIGS. 35 and 36 may be provided with constriction elements 134-2 configured to further secure an engagement between the needle guide 48-2 and a corresponding needle 38, 40 or needle hook 46 thereof. Specifically, each constriction element 134-2 may be provided with a widened feature configured to increase the integrity or lateral rigidity of each needle guide 48-2 when a needle 38, 40 is not inserted therethrough, such as when the suture 34-2 is being moved along the tracks 36 of the elongate member 22 of a suturing device 20, but also configured to effectively reduce the lateral rigidity of each needle guide 48-2 when a needle 38, 40 is received therethrough, such as during advancement through tissue and/or prosthetic material. As shown in FIGS. 35 and 36, for example, the widened feature of the constriction element 134-2, when in the non-deflected state, may substantially abut the inner walls of the needle guide 48-2, and thereby provide lateral support thereacross. When in the deflected state, the constriction element 134-2 may enable the needle guide 48-2 to substantially collapse and narrow so as to promote insertion or advancement thereof through a tissue, and the like. Furthermore, the constriction elements 134-2 may continue to provide lateral rigidity and support for the retention elements 132-2 once deployed and released into tissue and/or prosthetic material. For example, once the suture 34-2 is deployed and needle guides 48-2 are released, for instance cut, from the corresponding needles 38, 40, the constriction elements 134-2 may be configured to return to the non-deflected default state and thereby substantially prevent the retention elements 132-2 from collapsing and retracting from the tissue and/or prosthetic material.

Figure 37:
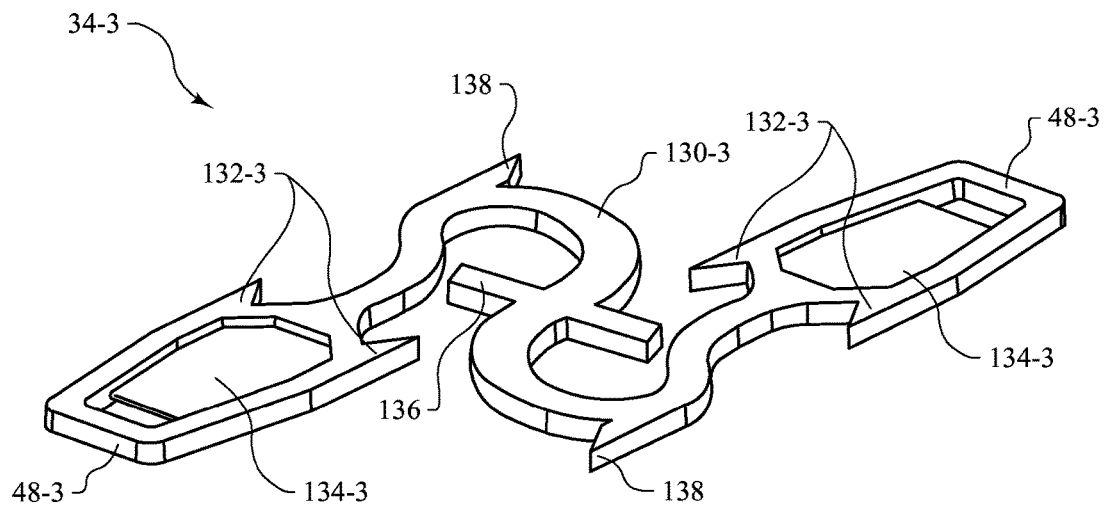
FIG. 37 is a perspective view of another exemplary embodiment of a fastener having constriction elements.
Figure 38:
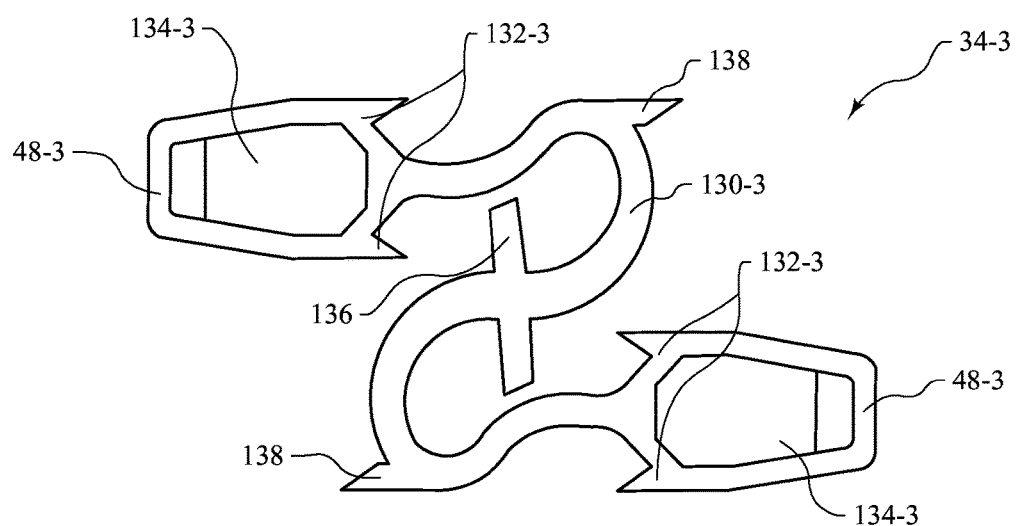
FIG. 38 is a top plan view of a fastener having constriction elements.

In still further alternatives, another exemplary embodiment of a tissue fastener or suture 34-3 is provided in FIGS. 37 and 38. As in previous embodiments, the suture 34-3 may generally comprise an elongated filament 130-3 extending between a first end and a second end, and at least one needle guide 48-3 disposed at one or more of the first and second ends of the elongated filament 130-3. The suture 34-3 may be formed of a material that is sufficiently flexible and compliant so as to be appropriately deployable by a suturing device 20, while also providing sufficient resilience or rigidity to maintain closure between tissue and/or prosthetic material upon deployment. The elongated filament 130-3 of the suture 34-3 may further include a cross member 136 as well as filament guides 138 configured to stabilize the suture 34-3 as it is moved within the tracks 36 and along the elongate member 22 of a suturing device 20. Additionally, any one or more of the cross member 136 and the filament guides 138 may be configured with retention features configured to aid in resisting retraction thereof once deployed into tissue and/or prosthetic material.

The needle guides 48-3 of FIGS. 37 and 38 may be sufficiently sized and configured to be engaged by a needle 38, 40 of a suturing device 20, or one of the needle hooks 46 thereof, while also being sufficiently thin or easily released from the needles 38, 40, for example, via any of the release mechanisms 124, 126 provided in FIGS. 24-27. The needle guides 48-3 may be provided with a relatively tapered tip, as well as provided with one or more retention elements 132-3, configured to facilitate advancement thereof through tissue and/or prosthetic material during deployment, and resist retraction thereof to promote a secure closure. Each of the needle guides 48-3 in FIGS. 37 and 38 may be provided with constriction elements 134-3 configured to further secure an engagement between the needle guide 48-3 and a corresponding needle 38, 40 or needle hook 46 thereof. Specifically, each constriction element 134-3 may be provided with a substantially webbed feature configured to increase the integrity or lateral rigidity of each needle guide 48-3 when a needle 38, 40 is not inserted therethrough, such as when the suture 34-3 is being moved along the tracks 36 of the elongate member 22 of a suturing device 20, but also configured to effectively reduce the lateral rigidity of each needle guide 48-3 when a needle 38, 40 is received therethrough, such as during advancement through tissue and/or prosthetic material. As shown in FIGS. 37 and 38, for example, the webbed feature of the constriction element 134-3, when in the non-deflected state, may provide rigidity and lateral support against the inner walls of the needle guide 48-3. When the constriction element 134-3 is at least partially deflected state due to the insertion of a needle 38, 40, the needle guide 48-3 may be enabled to substantially collapse and narrow so as to promote insertion or advancement thereof through a tissue, and the like. Furthermore, the constriction elements 134-3 may continue to provide lateral rigidity and support for the retention elements 132-3 once deployed and released into tissue and/or prosthetic material. For example, once the suture 34-3 is deployed and needle guides 48-3 are released, for instance cut, from the corresponding needles 38, 40, the constriction elements 134-3 may be configured to return to the non-deflected default state and thereby substantially prevent the retention elements 132-3 from collapsing and retracting from the tissue and/or prosthetic material.

Figure 39:
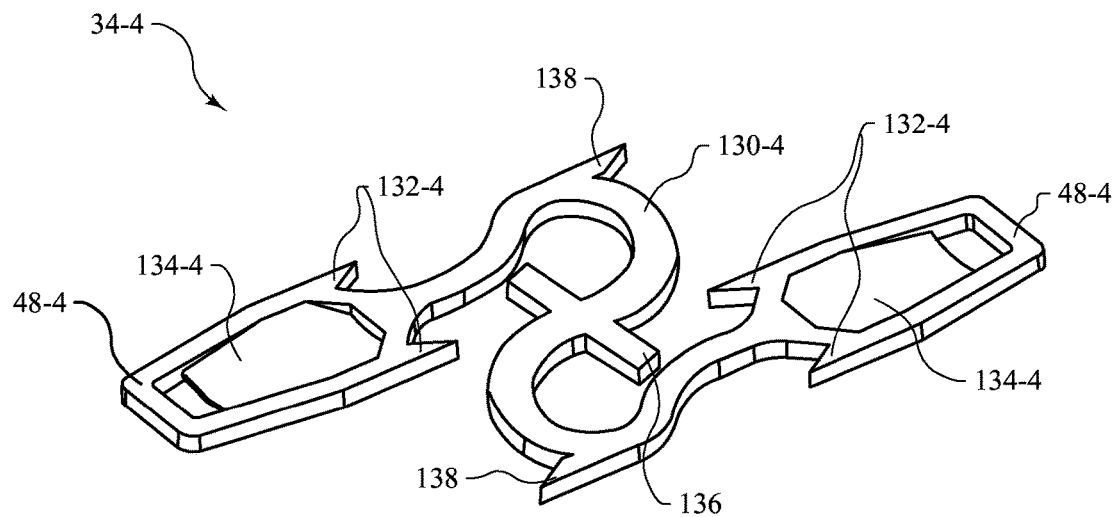
FIG. 39 is a perspective view of another exemplary embodiment of a fastener having constriction elements.
Figure 40:
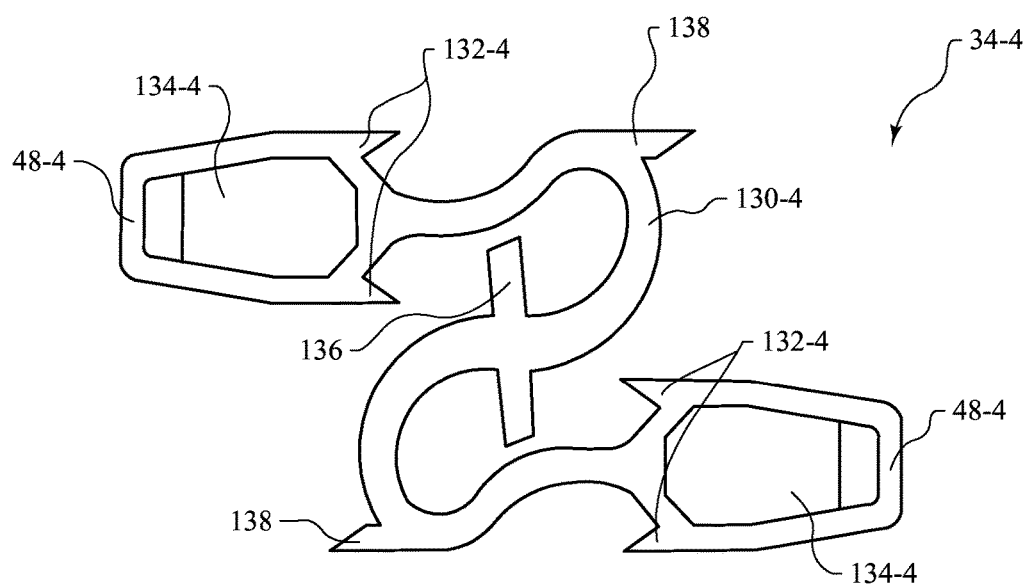
FIG. 40 is a top plan view of a fastener having constriction elements.

Referring now to FIGS. 39 and 40, another exemplary embodiment of a tissue fastener or suture 34-4 is provided. As in previous embodiments, the suture 34-4 may generally comprise an elongated filament 130-4 extending between a first end and a second end, and at least one needle guide 48-4 disposed at one or more of the first and second ends of the elongated filament 130-4. The suture 34-4 may be formed of a material that is sufficiently flexible and compliant so as to be appropriately deployable by a suturing device 20, while also providing sufficient resilience or rigidity to maintain closure between tissue and/or prosthetic material upon deployment. The elongated filament 130-4 of the suture 34-4 may further include a cross member 136 as well as filament guides 138 configured to stabilize the suture 34-4 as it is moved within the tracks 36 and along the elongate member 22 of a suturing device 20. Additionally, any one or more of the cross member 136 and the filament guides 138 may be configured with retention features configured to aid in resisting retraction thereof once deployed into tissue and/or prosthetic material.

The needle guides 48-4 of FIGS. 39 and 40 may be sufficiently sized and configured to be engaged by a needle 38, 40 of a suturing device 20, or one of the needle hooks 46 thereof, while also being sufficiently thin or easily released from the needles 38, 40, for example, via any of the release mechanisms 124, 126 provided in FIGS. 24-27. The needle guides 48-4 may be provided with a relatively tapered tip, as well as provided with one or more retention elements 132-4, configured to facilitate advancement thereof through tissue and/or prosthetic material during deployment, and resist retraction thereof to promote a secure closure. Each of the needle guides 48-4 in FIGS. 39 and 40 may be provided with constriction elements 134-4 configured to further secure an engagement between the needle guide 48-4 and a corresponding needle 38, 40 or needle hook 46 thereof. As in the suture 34-3 of FIGS. 37 and 38, the constriction elements 134-4 of FIGS. 39 and 40 may be provided with a webbed feature configured to increase the integrity or lateral rigidity of each needle guide 48-4 when a needle 38, 40 is not inserted therethrough, such as when the suture 34-4 is being moved along the tracks 36 of the elongate member 22 of a suturing device 20, but also configured to effectively reduce the lateral rigidity of each needle guide 48-4 when a needle 38, 40 is received therethrough, such as during advancement through tissue and/or prosthetic material. Unlike the previous suture 34-3, however, the constriction elements 134-4 of the suture 34-4 of FIGS. 39 and 40 may be arched or otherwise contrasted with the general plane of the suture 34-4 and biased to exert a lateral force against the inner walls of the needle guide 48-4 when in the non-deflected state. When the constriction element 134-4 is at least partially deflected due to the insertion of a needle 38, 40, the needle guide 48-4 may be enabled to substantially collapse and narrow so as to promote insertion or advancement thereof through a tissue, and the like. Furthermore, the constriction elements 134-4 may continue to provide lateral rigidity and support for the retention elements 132-4 once deployed and released into tissue and/or prosthetic material. For example, once the suture 34-4 is deployed and needle guides 48-4 are released, for instance cut, from the corresponding needles 38, 40, the constriction elements 134-4 may be configured to return to the non-deflected default state and thereby substantially prevent the retention elements 132-4 from collapsing and retracting from the tissue and/or prosthetic material.

Figure 41:
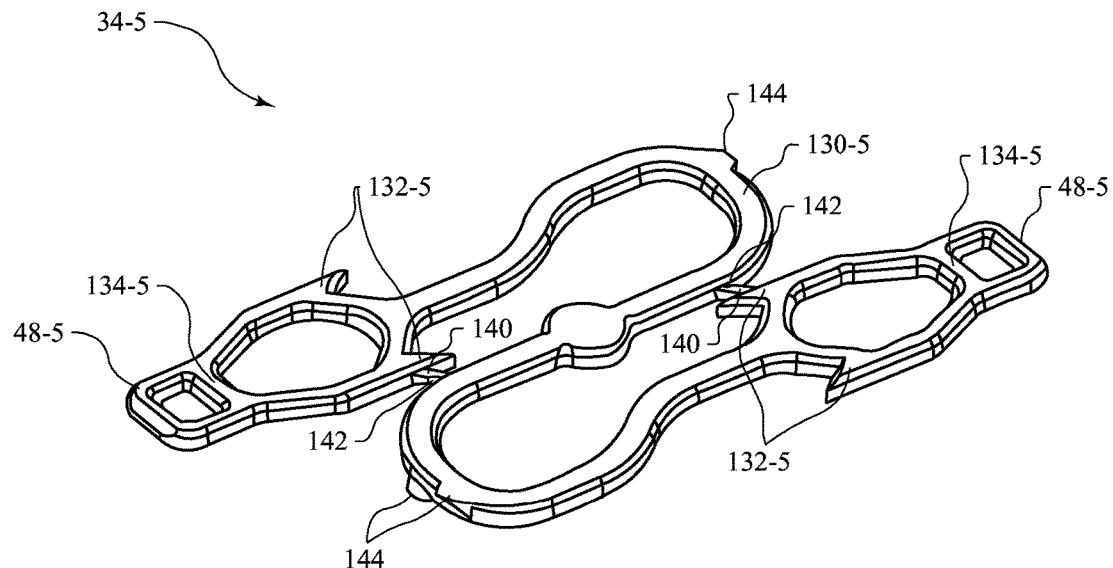
FIG. 41 is a perspective view of yet another exemplary embodiment of a fastener having constriction elements, breakaway tabs and nesting elements.
Figure 42:
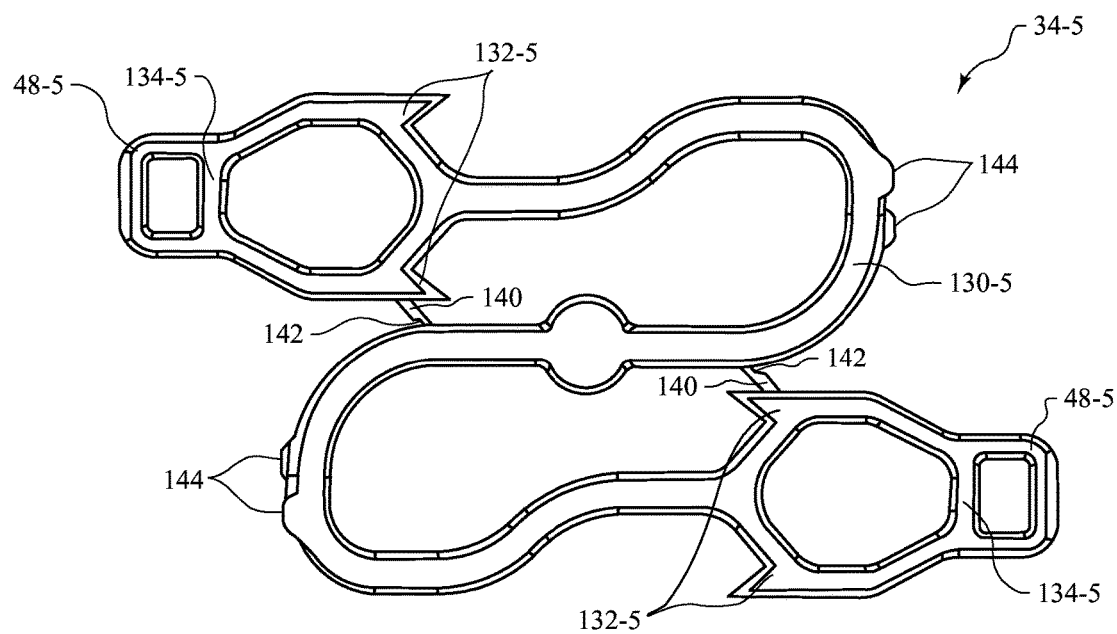
FIG. 42 is a top plan view of a fastener having constriction elements, breakaway tabs and nesting elements.

Referring further to FIGS. 41 and 42, yet another exemplary embodiment of a tissue fastener or suture 34-5 is provided. Similar to previous embodiments, the suture 34-5 may generally comprise an elongated filament 130-5 extending between a first end and a second end, and at least one needle guide 48-5 disposed at one or more of the first and second ends of the elongated filament 130-5. The suture 34-5 may be formed of a material that is sufficiently flexible and compliant so as to be appropriately deployable by a suturing device 20, while also providing sufficient resilience or rigidity to maintain closure between tissue and/or prosthetic material upon deployment. The elongated filament 130-5 of the suture 34-5 may also include breakaway tabs 140 configured to help stabilize the suture 34-5 as it is moved within the tracks 36 and along the elongate member 22 of a suturing device 20. As shown, each breakaway tab 140 may be coupled between a needle guide 48-5 and a corresponding section of the elongated filament 130-5 in the folded position, and configured to be detachable upon deployment. In particular, the breakaway tabs 140 may be sized and configured to provide, not only sufficient planar and lateral rigidity to the suture 34-5 prior to deployment, but also configured with sufficient detachability so as not to interfere with the deployment thereof. As better seen in FIG. 42, for example, each of the breakaway tabs 140 may incorporate attenuated features 142, such as in the form of grooves, slits, perforations, or the like. Furthermore, the breakaway tabs 140 may be angled or otherwise positioned relative to the needle guides 48-5 in a way to help resist retraction thereof once deployed into tissue and/or prosthetic material.

The needle guides 48-5 of FIGS. 41 and 42 may be sufficiently sized and configured to be engaged by a needle 38, 40 of a suturing device 20, or one of the needle hooks 46 thereof, while also being sufficiently thin or easily released from the needles 38, 40, for example, via any of the release mechanisms 124, 126 provided in FIGS. 24-27. The needle guides 48-5 may be provided with a relatively tapered tip, as well as provided with one or more retention elements 132-5, configured to facilitate advancement thereof through tissue and/or prosthetic material during deployment, and resist retraction thereof to promote a secure closure. As shown, the edges of the needle guides 48-5 may additionally be beveled, rounded, or otherwise configured to further facilitate advancement thereof. In addition, each of the needle guides 48-5 in FIGS. 41 and 42 may be provided with generally linear constriction elements 134-5 positioned to further secure an engagement between the needle guide 48-5 and a corresponding needle 38, 40 or needle hook 46 thereof. Moreover, the constriction elements 134-5 may serve to increase the integrity or lateral rigidity of each needle guide 48-5 when a needle 38, 40 is not inserted therethrough, such as when the suture 34-5 is being moved along the tracks 36 of the elongate member 22 of a suturing device 20. Furthermore, the constriction elements 134-5 may continue to provide lateral rigidity and support for the retention elements 132-5 once deployed and released into tissue and/or prosthetic material. For example, once the suture 34-5 is deployed and needle guides 48-5 are released from the corresponding needles 38, 40, the constriction elements 134-5 may be configured to prevent the retention elements 132-5 from collapsing and retracting from the tissue and/or prosthetic material.

Figure 43:
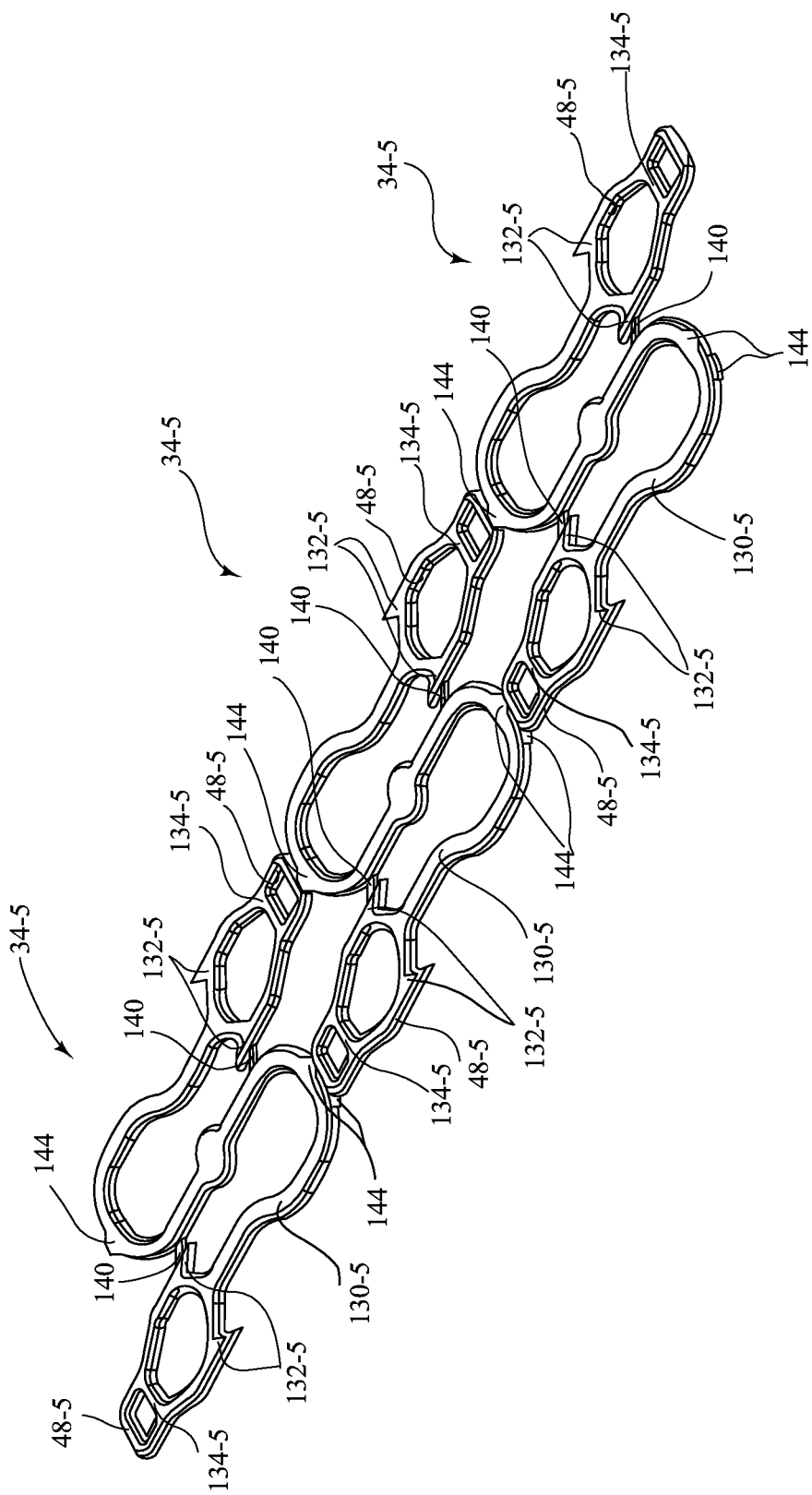
FIG. 43 is a perspective view of a string of fasteners, each having constriction elements, breakaway tabs and nesting elements.

In addition, the suture 34-5 of FIGS. 41 and 42 may further include one or more nesting elements 144, or extended features disposed along the elongated filament 130-5, which may be sized and configured to detachably couple to a counterpart section of an adjacent suture 34-5 in a string of sutures 34-5. As shown in FIG. 43, for example, each nesting element 144 may be configured to couple to the tip of the needle guide 48-5 of an adjacent suture 34-5. Correspondingly, the tips of each needle guide 48-5 may be beveled, rounded, or otherwise sized and shaped to be mateably received within the nesting elements 144 of an adjacent suture 34-5. In such a way, each suture 34-5 may include two sets of nesting elements 144, such as forward-facing nesting elements 144 for coupling to the trailing needle guide 48-5 of a preceding suture 34-5, and rearward-facing nesting elements 144 for coupling to the leading needle guide 48-5 of a subsequent suture 34-5. Furthermore, the nesting elements 144 may be coupled to corresponding sections of adjacent sutures 34-5 using, for example, flexible bonding material or adhesives, friction fitments, attenuated connections, or any other suitable arrangement that is, not only capable of maintaining rigidity of the string of sutures 34-5 prior to deployment, but also capable of being easily detached so as not to interfere with deployment.

From the foregoing, it can be seen that the present disclosure sets forth a medical fastening or suturing device adapted to rapidly and reliably install fasteners or sutures to secure tissue and/or any applicable prosthetic material. The device not only greatly reduces the time required for fastening tissues, but also results in improved ease of use relative to other methods. Furthermore, through the unique combination of elements set forth in the present disclosure, the tissue fastening or suturing is more reliably retained with reduced irritation and other complications to the patient and without adversely affecting the integrity of the attachment and/or closure.

What is claimed is:

1. A suturing device, comprising:
    a firing aperture having at least one needle rotatably disposed therein, the needle being configured to engage a suture for deployment;
    a drive mechanism operatively coupled to the needle and configured to advance the needle from a retracted position to an extended position during engagement, and retract the needle from the extended position to the retracted position during disengagement; and
    an autoloading mechanism operatively coupled to the drive mechanism and configured to slidably retrieve and position a suture to be deployed over the firing aperture after a prior suture has been deployed.

2. The suturing device of claim 1, wherein the needle includes a low-profile arcuate geometry configured to be substantially concealed within the firing aperture when in the retracted position and having maximized reach during advancement thereof, the needle further including a hook configured to engage a suture for deployment.

3. The suturing device of claim 1, wherein the firing aperture further includes a second needle rotatably disposed therein configured to engage a suture for deployment, the drive mechanism being configured to advance and retract the first and second needles in substantially equal increments but in opposing directions.

4. The suturing device of claim 1, wherein the drive mechanism includes a multi-bar linkage that is operatively coupled to the needle, each multi-bar linkage having at least a drive link and an intermediate link coupled between the drive link and the needle.

5. The suturing device of claim 1, wherein the autoloading mechanism includes a shuttle slidably disposed in communication between the firing aperture and one or more successively deployable sutures, the shuttle being configured to automatically retrieve one of the deployable sutures during deployment of a prior suture, and position the deployable suture over the firing aperture upon full deployment of the prior suture.

6. The suturing device of claim 1, wherein the autoloading mechanism includes a shuttle slidably disposed in communication between the firing aperture and one or more successively deployable sutures, the autoloading mechanism further including a spring configured to bias the shuttle toward the firing aperture, and a shuttle pawl coupled to the drive mechanism configured to pull the shuttle toward the deployable sutures during disengagement of the drive mechanism until at least the shuttle engages one of the deployable sutures, the shuttle pawl releasing the shuttle and enabling the spring to send the shuttle and the engaged suture to the firing aperture upon full deployment of a prior suture.

7. The suturing device of claim 6, wherein the autoloading mechanism further includes a declutch feature for releasing the shuttle from the shuttle pawl, the declutch feature being positioned relative to the shuttle pawl such that the declutch feature declutches the shuttle pawl from the shuttle at least once one of the deployable sutures is engaged and the prior suture is fully deployed.

8. The suturing device of claim 6, wherein the shuttle further includes one or more suture pawls for engaging one of the deployable sutures, the suture pawls being configured to be engaging when the shuttle moves toward the firing aperture and non-engaging when the shuttle moves away from the firing aperture, the suture pawls being configured to position an engaged suture on the firing aperture such that a needle guide of the suture is aligned with and engageable by the needle during deployment.

9. The suturing device of claim 1, wherein the firing aperture includes a release mechanism configured to release an engaged suture from the needle during disengagement of the drive mechanism.

10. The suturing device of claim 1, wherein the firing aperture includes a release mechanism having a cutting edge disposed within the firing aperture and proximate to the needle in the retracted position, the cutting edge being positioned such that an engaged suture is cut and released from the needle when the needle returns to the retracted position.

11. The suturing device of claim 1, wherein the firing aperture includes a plurality of needles rotatably disposed therein configured to engage a suture for deployment, the drive mechanism being configured to advance and retract the plurality of needles.

12. A suturing device, comprising:
an elongate member extending between a working end and a control end and having a track for receiving one or more deployable sutures therein, the working end having a firing aperture disposed in communication with the track and a distal needle and a proximal needle rotatably disposed therein;
a drive mechanism disposed within the elongate member and operatively coupling the control end with each of the distal and proximal needles, the drive mechanism being configured to advance each of the distal and proximal needles from a retracted position to an extended position during engagement, and retract each of the distal and proximal needles from the extended position to the retracted position during disengagement; and
an autoloading mechanism disposed along the elongate member and proximate the working end, the autoloading mechanism operatively coupled to the drive mechanism and configured to slidably retrieve and position one of the deployable sutures over the firing aperture for deployment after a prior suture has been deployed.

13. The suturing device of claim 12, wherein the drive mechanism includes at least a distal drive link operatively coupled to the distal needle and a proximal drive link operatively coupled to the proximal needle, the distal and proximal drive links being configured to advance and retract the distal and proximal needles in substantially equal increments but in opposing directions.

14. The suturing device of claim 13, wherein the distal drive link is pivotally coupled to the distal needle via at least a distal intermediate link and the proximal drive link is pivotally coupled to the proximal needle via at least a proximal intermediate link.

15. The suturing device of claim 13, wherein the control end includes a triggering mechanism for operating the drive mechanism, the triggering mechanism including at least a reversing lever coupled to each of the distal and proximal drive links, the reversing lever being configured to drive the distal and proximal drive links and the corresponding distal and proximal needles in substantially equal increments but in opposing directions in response to triggering actions received at the control end.

16. The suturing device of claim 13, wherein the control end includes a triggering mechanism having a handle that is operable in one of an engaging motion and a disengaging motion, the triggering mechanism being configured such that operating the handle in the engaging motion slidably drives the distal drive link toward the working end and the proximal drive link toward the control end, and operating the handle in the disengaging motion slidably drives the distal drive link toward the control end and the proximal drive link toward the working end, the triggering mechanism being configured to drive the distal and proximal drive links and the corresponding distal and proximal needles in substantially equal increments but in opposing directions.

17. The suturing device of claim 13, wherein at least one of the distal drive link and the proximal drive link includes a plurality of catches incrementally disposed thereon, and the autoloading mechanism includes a pusher slidably disposed along the track having one or more pusher tabs extending therefrom, the pusher tabs being configured to unidirectionally interface with the catches such that engaging any one or more of the distal drive link and the proximal drive link also moves the pusher toward the firing aperture.

18. The suturing device of claim 12, wherein the autoloading mechanism includes a shuttle slidably disposed along the track of the elongate member in communication between the firing aperture and one or more deployable sutures, the shuttle being configured to automatically retrieve one of the deployable sutures during deployment of a prior suture, and position the deployable suture over the firing aperture upon full deployment of the prior suture.

19. The suturing device of claim 12, wherein the autoloading mechanism includes a shuttle slidably disposed along the track of the elongate member in communication between the firing aperture and one or more deployable sutures, the autoloading mechanism further including a spring disposed within the elongate member and configured to bias the shuttle toward the firing aperture, and a shuttle pawl coupled to the distal drive link configured to pull the shuttle toward the one or more deployable sutures during disengagement of the drive mechanism until at least the shuttle engages one of the deployable sutures, the shuttle pawl releasing the shuttle and enabling the spring to send the shuttle and the engaged deployable suture to the firing aperture upon full deployment of a prior suture.

20. The suturing device of claim 19, wherein the autoloading mechanism further includes a declutch feature for releasing the shuttle from the shuttle pawl, the declutch feature being fixedly disposed within the elongate member relative to the shuttle pawl such that the declutch feature declutches the shuttle pawl from the shuttle at least once one of the deployable sutures is engaged and the prior suture is fully deployed.

21. The suturing device of claim 19, wherein the shuttle further includes one or more suture pawls for engaging with one of the deployable sutures, the suture pawls being configured to be engaging when the shuttle moves toward the firing aperture and non-engaging when the shuttle moves away from the firing aperture, the suture pawls being configured to position an engaged suture on the firing aperture such that one or more needle guides of the suture is aligned with and engageable by at least one of the distal and proximal needles during deployment.

22. The suturing device of claim 12, wherein the firing aperture includes a release mechanism having a distal cutting edge disposed within the firing aperture proximate to the distal needle in the retracted position, and a proximal cutting edge disposed within the firing aperture proximate to the proximal needle in the retracted position, the distal and proximal cutting edges being positioned such that an engaged suture is cut and released from the distal and proximal needles when the distal and proximal needles return to the corresponding retracted positions during disengagement of the drive mechanism.

* * * * *